US007933763B2

(12) United States Patent
Lawson et al.

(10) Patent No.: US 7,933,763 B2
(45) Date of Patent: Apr. 26, 2011

(54) METHOD AND SOFTWARE FOR EXTRACTING CHEMICAL DATA

(75) Inventors: Alexander Johnston Lawson, Waldems-Reichenbach (DE); Stefan Roller, Wiesbaden (DE); Helmut Grotz, Frankfurt am Main (DE); Janusz L. Wisniewski, Frankfurt am Main (DE); Libuse Goebels, Kelkheim (DE)

(73) Assignee: MDL Information Systems, GmbH, Frankfurt (DE)

( * ) Notice: Subject to any disclaimer, the term of this patent is extended or adjusted under 35 U.S.C. 154(b) by 367 days.

(21) Appl. No.: 10/836,374

(22) Filed: Apr. 30, 2004

(65) Prior Publication Data

US 2005/0246316 A1 Nov. 3, 2005

(51) Int. Cl.
*G06F 17/28* (2006.01)
(52) U.S. Cl. ............... 704/2; 706/45; 706/48; 704/4; 704/9; 715/205
(58) Field of Classification Search .................. None
See application file for complete search history.

(56) References Cited

U.S. PATENT DOCUMENTS

| 6,182,029 | B1 * | 1/2001 | Friedman ............ 704/9 |
| 7,054,754 | B1 * | 5/2006 | Brecher ............ 702/19 |
| 2002/0004792 | A1 | 1/2002 | Busa |
| 2002/0087508 | A1 | 7/2002 | Hull et al. |

FOREIGN PATENT DOCUMENTS

| GB | 2228115 | 8/1990 |
| WO | WO 02/33587 | 4/2002 |
| WO | WO 2005/050475 | 6/2005 |

OTHER PUBLICATIONS

Diky et al., J. Chem. Inf. Comput. Sci., vol. 43, 15-24, 2003.*
Vander Stouw et al., J. Chem. Doc., vol. 7, No. 3, p. 165-169, 1967.*
Murray-Rust et al., New J. Chem., vol. 25, p. 618-634, 2001.*
Postma et al., J. Chem. Inf. Comput. Sci., vol. 36, No. 4, p. 770-785, 1996.*
Akutsu (RECOMB'03, Apr. 10-13, 2003, p. 1-8).*
Holliday et al (J. Chem. Inf. Comput. Sci., vol. 32, p. 453-462, 1992).*
Frenkel et al. (Journal of Chemical and Engineering Data, vol. 48, No. 1, p. 2-13, 2003, online Dec. 17, 2002).*
Cooke-Fox et al. [Cooke-Fox et al. A] (J. Chem. Inf. Comput. Sci., vol. 29, p. 101-105, 1989).*
Cooke-Fox et al. [Cooke-Fox et al. B] (J. Chem. Inf. Comput. Sci., vol. 29, p. 106-112, 1989).*
Cooke-Fox et al. [Cooke-Fox et al. C] (J. Chem. Inf. Comput. Sci., vol. 29, p. 112-118, 1989).*
Castano et al. (In Proceedings of the International Symposium on Reference Resolution for NLP (2002), pp. 9).*
Zamora et al. (J. Chem. Inf. Comput. Sci. 1984, 24, 176-181).*
Brecher J: "Name=Struct: A Practical Approach to the Sorry State of Real-Life Chemical Nomenclature", Journal of Chemical Information and Computer Sciences, vol. 39, No. 6, Nov. 1999, pp. 943-950.
Cooke-Fox D I et al: "Computer translation of IUPAC systematic organic chemical nomenclature. 4. Concise connection tables to structure diagrams", Journal of Chemical Information and Computer Sciences USA, vol. 30, No. 2, May 1990. pp. 122-127, ISSN: 0095-2338.
Debruijn B & Martin J: "Getting to the (c)ore of knowledge: mining biomedical literature", Int.J.Med.Inform., 2002, 67 (1-3) 7-18.
Gkoutos G et al: "ChemDig: new approaches to chemically significant indexing and searching of distributed web collections", New Journal of Chemistry, vol. 26, 2002, pp. 656-666, available at http://www.rsc.org/Publishing/Journals/NJ/article.asp?doi=b110693g.
Hirschman L et al "Rutabaga by any other name: extracting biological names", J.Biomed.Inform., 2002, 35 (4) 247-59.
Ibison P et al: "Chemical Literature Data Extraction: the CLiDE project", Journal of Chemical Information and Computer Sciences USA, vol. 33, No. 3, May 1993, pp. 338-344, ISSN: 0095-2338.
Kemp N et al: "Extraction of information from the text of chemical patents. 1. Identification of specific chemical names", Journal of Chemical Information and Computer Sciences ACS US, vol. 38, No. 4, Jul. 1998, pp. 544-551, ISSN 0095-2338.
Mika et al: Protein names precisely peeled off text, Bioinformatics, vol. 20, supp. 4, Aug. 2004, pp. i241-i247, available from http://bioinformatics.oxfordjournals.org/cgi/reprint/20/suppl_1/i241.
Rzhetsky A et al: "GeneWays: a system for extracting, analyzing, visualizing, and integrating molecular pathway data", J.Biomed.Inform., Feb. 2004, 37(1) 43-53.
Vander Stouw G G et al: "Automated conversion of chemical substance names to atom-bond connection tables", Journal of Chemical Documentation USA, vol. 14, No. 4, Nov. 1974, pp. 185-193, ISSN: 0021-9576.
Wilbur W J et al: "Analysis of biomedical text for chemical names: a comparison of three methods", Proceedings/AMIA ... Annual Symposium, AMIA Symposium, 1999, pp. 176-180, ISSN: 1531-605X.
Williams A: "ACD/Name: Completing the Cycle Between Systematic Names and Chemical Structures", ACD Users Meeting [Online] May 2002, available at http://www.acdlabs.com/download/publ/2002/naum2002/naming.pdf.

* cited by examiner

*Primary Examiner* — Karlheinz R Skowronek
(74) *Attorney, Agent, or Firm* — Troutman Sanders, LLP

(57) ABSTRACT

Preferred embodiments of the present invention comprise methods and software for processing text documents and extracting chemical data therein. Preferred method embodiments comprise: (a) identifying and tagging one or more chemical compounds within a text document; (b) identifying and tagging physical properties related to one or more of those compounds; (c) translating one or more of those compounds into a chemical structure; (d) identifying and tagging one or more chemical reaction descriptions within the text document; and (e) extracting at least some of the tagged information and storing it in a database.

17 Claims, 17 Drawing Sheets

Example 4.1.6
4,4'-Bis(bromomethyl)-1,1'-biphenyl 4,4'-Bis-methyl-1,1'-biphenyl (5.00 g, 27.4 mmol), *N-bromosuccinimide* (9.75 g, 54.8 mmol) and α,α'-azoisobutyronitrile (50 mg, as initiator) were heated to reflux at 76°C in dry CCl4 (100 mL) with stirring for 18 h in the presence of bright light. With two spots predominant by tlc the reaction was ceased and the mixture filtered to remove the *succinimide* and the filtrate washed with distilled H2O and dried over *MgSO4*.
The solvent was removed under reduced pressure.
Solids were recrystallized seven times from hot *dichloromethane/hexane* to give the title compound as white crystalline flakes (2.32 g, 22%), mp 167-169°C (lit. 171-173°C) δH(250 MHz; *CDCl3*) 4.54 (*4H*, s, *CH2*) and 7.57-7.44 (*8H*, dd, J=7.5, 22.8 Hz, *Ar*), δC(62.9 MHz; *CDCl3*) 33.3, 127.5, 129.6, 137.2 and 140.6; m/z 339.9 (M+, 100%).

product        starting material
reagent          solvent

FIG. 3

| | | |
|---|---|---|
| 402 | Reaction RN<br>Reactant PRN<br>Product PRN<br>Reagent PRN<br>Solvent PRN<br>Yield | <u>8</u><br><u>92817</u> 5-nitro-isoquinoline<br><u>52974</u> 5,8-dinitro-isoquinoline<br><u>93401</u> potassium nitrate<br><u>33694</u> concentrated sulphuric acid<br>0.6g |
| 404 | 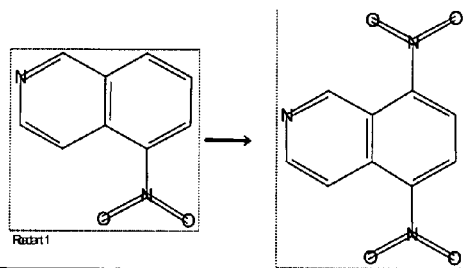 | |
| 406 | Example Text | EXAMPLE 6<br><br>This example illustrates the preparation of 5,8-dinitro-I soquinoline having the formula: SPC12<br><br>5-nitro-isoquinoline (5 g) was dissolved in concentrated sulphuric acid (50 ml) and potassium nitrate (10 g) was added. The mixture was then heated at 180.deg.C for seven hours, allowed to cool to room temperature (20.deg.C), and then poured onto 100 ml of an ice/water mixture.<br><br>This aqueous reaction mixture was made alkaline with ammonia, and then extracted with methylene dichloride. The methylene dichloride extract was dried, the solvent was evaporated off, and the residue thus obtained was recrystallized from benzene, to yield 0.6 g of product melting at 241.deg. - 242.deg.C. |
| 408 | Ref. 1<br>Publ.: | Frontpage/Claim: <u>8</u>; Fulltext: <u>LitLink</u>; ICI Australia Limited;<br><br>US03930837 A1 (1976/01/06), Appl.: US3149102 (1972/12/14) |

FIG. 4

1,1-dimethoxy-2-[1-methyl-1-phenyl-ethoxy]-ethane or [1-methyl-1-phenyl-ethoxy]-acetaldehyde dimethyl acetal or (α,α-dimethylbenzyloxy)-acetaldehyde dimethyl acetal or [(2,2-dimethoxyethoxy)-1-methylethyl]benzene (CAS name)

4-adamantan-2-yl-benzo[d][1,3]oxazin-2-one (Beilstein/AutoNom)
4-tricyclo[3.3.1.1^{3,7}]decan-2-yl-3,1-benzoxazin-2-one (CAS/IUPAC)
4-(2-adamantyl)-2H-3,1-benzoxazin-2-one ethylene diamine tetra acetic acid
ethylenediamine tetracetic acid
ethylene-tetraacetic acid
ethylene(diamine)tetraacetic acid
tetraacetic acid-ethylene to upper fragment

3.2.1 2,2-Dimethyl-5-(4-pentenyl)-1,3-dioxane-4,6-dione (10)

Ethylene diammonium diacetate (EDDA) (248 mg, 1.4 mmol) was added to a solution of Meldrum's acid (1.188 g, 8.5 mmol) and 4-pentenal (460 mg, 5.5 mmol) in absolute EtOH (6.6 mL) at rt and the resulting solution was stirred for 1 h. $BH_3 \cdot NH(CH_3)_2$ (326 mg, 5.5 mmol) was added to the reaction, which was stirred for 17.5 h. Water (35 mL) and 5% aqueous HCl solution (3 mL) were added to the reaction, which was extracted with $CH_2Cl_2$ (3×20 mL). The combined organic layers were dried ($MgSO_4$) and concentrated to give 1.47 g of crude product. Flash chromatography (9:1 hexanes/EtOAc containing 0.5% HOAc) gave 805 mg (69%) of pure 10 as a white solid: mp 48–50°C; $^1H$ NMR 5.80 (ddt, 1, J=17.1, 10.4, 6.1 Hz), 5.04 (d, 1, J=17.1 Hz), 4.99 (d, 1, J=10.4 Hz), 3.52 (t, 1, J =4.9 Hz), 2.17–2.10 (m, 4), 1.79 (s, 3), 1.76 (s, 3), 1.61-1.53 (m, 2); $^{13}C$ NMR 165.5 (2C), 137.7, 115.2, 104.8, 46.1, 33.5, 28.4, 26.1, 25.6.

Formal structure

FIG. 12

3.2.1
2,2-Dimethyl-5-(4-pentenyl)-1,3-dioxane-4,6-dione (10)

Ethylene diammonium diacetate (EDDA) (248 mg, 1.4 mmol) was added to a solution of Meldrum's acid (1.188 g, 8.5 mmol) and 4-pentenal (460 mg, 5.5 mmol) in absolute EtOH (6.6 mL) at rt and the resulting solution was stirred for 1 h. BH$_3$·NH(CH$_3$)$_2$ (329 mg, 5.5 mmol) was added to the reaction, which was stirred for 17.5 h. Water (35 mL) and 5% aqueous HCl solution (3 mL) were added to the reaction, which was extracted with CH$_2$Cl$_2$ (3×20 mL). The combined organic layers were dried (MgSO$_4$) and concentrated to give 1.47 g of crude product. Flash chromatography (9:1 hexanes/EtOAc containing 0.5% HOAc) gave 805 mg (69%) of pure 10 as a white solid: mp 48-50°C; $^1$H NMR 5.80 (ddt, 1, J=17.1, 10.4, 6.1 Hz), 5.04 (d, 1, J=17.1 Hz), 4.99 (d, 1, J=10.4 Hz), 3.52 (t, 1, J=4.9 Hz), 2.17-2.10 (m, 4), 1.79 (s, 3), 1.75 (s, 3), 1.61-1.53 (m, 2); $^{13}$C NMR 165.5 (2C), 137.7, 115.2, 104.8, 46.1, 33.5, 28.4, 26.9, 26.1, 25.6.

Physical properties

FIG. 13

3.2.1 2,2-Dimethyl-5-(4-pentenyl)-1,3-dioxane-4,6-dione (10)

Ethylene diammonium diacetate (EDDA) (248 mg, 1.4 mmol) was added to a solution of Meldrum's acid (1.188 g, 8.5 mmol) and 4-pentenal (460 mg, 5.5 mmol) in absolute EtOH (6.6 mL) at rt and the resulting solution was stirred for 1 h. BH$_3$·NH(CH$_3$)$_2$ (326 mg, 5.5 mmol) was added to the reaction, which was stirred for 17.5 h. Water (35 mL) and 5% aqueous HCl solution (3 mL) were added to the reaction, which was extracted with CH$_2$Cl$_2$ (3×20 mL). The combined organic layers were dried (MgSO$_4$) and concentrated to give 1.47 g of crude product. Flash chromatography (9:1 hexanes/EtOAc containing 0.5% HOAc) gave 805 mg (69%) of pure 10 as a white solid: mp 48–50°C; $^1$H NMR 5.80 (ddt, 1, J=17.1, 10.4, 6.1 Hz), 5.04 (d, 1, J=17.1 Hz), 4.99 (d, 1, J=10.4 Hz), 3.52 (t, 1, J=4.9 Hz), 2.17–2.10 (m, 4), 1.79 (s, 3), 1.76 (s, 3), 1.61–1.53 (m, 2); $^{13}$C NMR 165.5 (2C), 137.7, 115.2, 104.8, 46.1, 33.5, 28.4, 26.9, 26.1, 25.6.

FIG. 14

3.2.1
2,2-Dimethyl-5-(4-pentenyl)-1,3-dioxane-4,6-dione (10)

Ethylene diammonium diacetate (EDDA) (248 mg, 1.4 mmol) was added to a solution of Meldrum's acid (1.188 g, 8.5 mmol) and 4-pentenal (460 mg, 5.5 mmol) in absolute EtOH (6.6 mL) at rt and the resulting solution was stirred for 1 h. $BH_3 \cdot NH(CH_3)_2$ (326 mg, 5.5 mmol) was added to the reaction, which was stirred for 17.5 h. Water (35 mL) and 5% aqueous HCl solution (3 mL) were added to the reaction, which was extracted with $CH_2Cl_2$ (3×20 mL). The combined organic layers were dried ($MgSO_4$) and concentrated to give 1.47 g of crude product. Flash chromatography (9:1 hexanes/EtOAc containing 0.5% HOAc) gave 805 mg (69%) of pure 10 as a white solid: mp 48–50°C; $^1$H NMR 5.80 (ddt, 1, J=17.1, 10.4, 6.1 Hz), 5.04 (d, 1, J=17.1 Hz), 4.99 (d, 1, J=10.4 Hz), 3.52 (t, 1, J =4.9 Hz), 2.17–2.10 (m, 4), 1.79 (s, 3), 1.76 (s, 3), 1.61–1.53 (m, 2); $^{13}$C NMR 165.5 (2C), 137.7, 115.2, 104.8, 46.1, 33.5, 28.4, 26.9, 26.1, 25.6.

Labels, Abbreviations, Anaphor 

FIG. 15

{-}[EX_]3.2.1
{-}[P#STR60-normal] 2,2-Dimethyl-5-(4-pentenyl)-1,3-dioxane-4,6-dione {-}[IC60] (10)
{-}[E#STR61-REACTANT] ethylene diammonium diacetate {-}[IC61] (EDDA) (248 mg, 1.4 mmol) was added to a solution of {-}[E#STR20-REACTANT] meldrum's acid (1.188 g, 8.5 mmol) and {-}[E#STR23-REACTANT] 4-pentenal (460 mg, 5.5 mmol) in absolute {-}[S#STR17-SOLVENT] EtOH (6.6 mL) at rt and the resulting solution was stirred for 1 h. {-}[E-REACTANT] BH$_3$·NH(CH$_3$)$_2$ (326 mg, 5.5 mmol) was added to the reaction, which was stirred for 17.5 h. {-}[S#STR62-REACTANT] water (35 mL) and 5% {-}[A-REACTANT] aqueous HCl solution (3 mL) were added to the reaction, which was extracted with {-}[X] CH$_2$Cl$_2$ (3*20 mL). The combined organic layers were dried ({-}[X] MgSO$_4$) and concentrated to give {-}[YIELD_VALm] 1.47 g of crude {-} [ANAPHORIC_PRODUCT] product. Flash chromatography (9:1 {-}[X-class] hexanes / {-}[X-normal] EtOAc containing 0.5% HOAc) gave {-}[YIELD_VALm] 805 mg (69%) of pure {-}[COMP-PRODUCT] 10 as a white {-} [ANAPHORIC_PRODUCT] solid : mp 48-50°C; {-}[NMR_NUC] 1H NMR 5.80 (ddt, 1, J=17.1, 10.4, 6.1 Hz), 5.04 (d, 1, J=17.1 Hz), 4.99 (d, 1, J=10.4 Hz), 3.52 (t, 1, J=4.9 Hz), 2.17-2.10 (m, 4), 1.79 (s, 3), 1.76 (s, 3), 1.61-1.53 (m, 2); {-}[NMR_NUC] 13C NMR 165.5 (2C), 137.7, 115.2, 104.8, 46.1, 33.5, 28.4, 26.9, 26.1, 25.6.

FIG. 17

METHOD AND SOFTWARE FOR EXTRACTING CHEMICAL DATA

BACKGROUND

Names, chemical formulas and structure diagrams are the language of chemistry. In any subject where objects can be expressed in a variety of languages, there is an interest in and a need for translation between the different expressions that describe those objects. A need for nomenclature arises when chemists have to communicate the information on compounds by spoken or written word, in the latter case usually where a structural diagram (unambiguous and unique) is for some reason inappropriate or cannot be used.

The nomenclature used to describe chemical structures is a language and thus may be handled, when translated into another representation, using methods of linguistics[1-3]. The human mental process for arriving at the structure from a chemical name appears to be a rule-based linguistic approach. As in linguistics, there is a struggle between pragmatists, who regard as satisfactory any word that conveys the intended meaning, and the purists, who insist that rules ought to be followed, with, unfortunately for the computer, the pragmatist having the advantage. Thus, the dedicated organizational body, Commission on the Nomenclature of Organic Chemistry (CNOC) by the International Union of Pure and Applied Chemistry (IUPAC) (http://www.iupac.org) which since 1938 has been responsible for inventing, monitoring, and revising the recommendations that are guidelines to the systematic nomenclature tries to see nomenclature as a whole, codifying already existing usage into rules and only very occasionally suggesting novelties.[4] Though the system has been developed over 110 years (initiated by the historical "Geneva Conference" in 1892), it is far from perfect and has not become a universal standard.[5]

In the meantime the CNOC ceased to exist and was replaced (in January 2002)—also within IUPAC—by the Division of Chemical Nomenclature and Structure Representation http://www.iupac.org/divisions/VIII/) whose main tasks are to co-ordinate efforts at nomenclature systematization and to supervise all relevant activities and projects of the chemical community directed toward unambiguous structure representation(s). Typically this includes computer representation[6-8] for local computing as well as for distributed computing in intranets and Internet (mainly web-based).

For the purpose of clarity in the selection of preferred names, the two most important producers and distributors of chemical information (Chemical Abstract Service (www dot cas dot com) and Beilstein Institute (the Beilstein file is now provided and maintained by MDL—at www dot mdli dot com)) devised non-documented ad hoc sub-rules, which only amplified the problem of uniquely naming organic compounds. These rules were necessary since IUPAC recommendations frequently allow more than one name for a given chemical compound. As a result, both institutions revised the IUPAC system and created their own "systematic" IUPAC-compatible (rather than IUPAC-sanctioned) nomenclatures. In addition, trivial and trade names, being shorter and more concise, have successfully replaced systematic names for a number of chemical compounds which are of commercial importance or are the subject of public concern 9, e.g., pharmaceuticals, insecticides, and pollutants). Both CAS and Beilstein claim to conform to the IUPAC rules, and in general this is true. The IUPAC recommendations were consciously formulated to allow considerable freedom in their application, and in many cases are not fully defined to their logical conclusion. In practice, this means that any given structure does not necessarily relate to one unique correct name. Thus, the specific "dialects" supported by CAS and Beilstein can still represent systematic nomenclature no matter how far apart they are. This, as far as computer usage is concerned, is the greatest weakness of the nomenclature.

The average user cannot find clearly defined "dialects" of IUPAC. This has also hindered solving the difficulties in establishing an unambiguous nomenclature standard. As long as such a standard does not exist, the practicing chemist will find himself to a great extent alienated from systematic nomenclature. But even if a sort of consensus is achieved and an unambiguous nomenclature standard is worked out and adopted, there is still the problem of nomenclature complexity. It is generally accepted that IUPAC nomenclature is cumbersome, with a very large number of rules, which are often very difficult to follow. Frequent alternatives allowed in name assignment, contradictory recommendations, the lack of rules in certain areas, and the exaggerated freedom in interpretation of the rules lead to ambiguity and specific nomenclature chaos.

One basic problem of naming is that a correct name is not necessarily the only correct name for a structure. To complicate matters, the rules for arriving at a correct name, as discussed above, are complex, and very few chemists can handle them. Even worse, the important centers for chemical documentation in the world are not uniform, either internally or externally, in their treatment of the rules. This is not the result of carelessness or lack of effort; it is simply a reflection of the difficulty on agreeing how a multi-dimensional problem can be forced into a single, universal text description. The structure shown in FIG. 5 illustrates the problem.

In principle, there is nothing wrong with a multiplicity of names for structures. As long as each name is an adequate representation of the structure, there are few real problems, apart from ensuring that chemists are reasonably familiar with the rules in a passive sense (i.e., can interpret a name, as opposed to creating one). However, the traditional (attempted) use of nomenclature has been much greater in its scope. Before computerization, the ideal was to index each significant structural sub-unit of the structure using nomenclature. The structure should be intuitively broken down into areas of relevance (acetaldehyde, benzene, ethane) and these are bound together into a text by use of locational parameters (1, 2, α). This approach is based on chemical experience, and is by no means bad. But it contains the limits of its own applicability insofar as the vocabulary used has never been fully standardized in a strictly defined sense, and the intuitive subdivision has never been fully cleared of internal contradictions. This has meant that the use of indices based on names or parts of names remains to this day a hazardous business. To use the above example, it is not immediately obvious to most chemists whether they should be looking under A (for acetaldehyde), B (for benzene), or E (for ethane). A computer system able to generate names algorithmically, and using the same rules of relevance would lead always to the same index name, thus solving the problem once and for all[7]. Such names could be then reversibly and unambiguously translated back into the same structural diagram.

This is unfortunately not the case at all. Systematic nomenclature as recommended by IUPAC failed to become a standard. As discussed above, trivial or trade names, being shorter and more concise, have successfully replaced systematic names for a number of chemical compounds which are of commercial importance or the subject of public concern. Any comprehensive computer program designed to deal with real-life chemical nomenclature has to be able to convert semi systematic, asystematic, obsolete, ambiguous, and otherwise "corrupted" names that are the reality of present chemical communication.

Translation of chemical names into structures can in general be treated as a problem of computerized syntactic and semantic analysis of nomenclature as an artificial language. In order to achieve such an analysis, a formal grammar of nomenclature must first be derived from informal rules. From the linguistic point of view, it is an interesting observation that the basic language of all naming systems in organic chemistry is essentially the same. While two chemists will name the same compound differently, both will be able to draw the same structural diagram. In this sense, the above-mentioned use of different naming practices corresponds to the problem of handling dialects, rather than a treatment of separate and distinct languages.

The knowledge of formal grammar of the chemico-linguistic requires the creation of a dictionary of fragments (so called morphemes) from which the names can be built, and the elucidation of appropriate syntax rules to govern that building.[2] The fragments are then grouped into numbered classes, and rules written in terms of these to define phrases so that each rule is referred to by its associated phrase name. For example, one rule can simultaneously allow for the fragments "meth,", "eth", "prop", etc., in the same context. The morphemes must then be localized and recognized within a supplied name. The process includes first parsing the name by breaking it into longest possible text fragments and then submitting the fragments to lexical analysis in order to identify the fragments, according to a set of syntax rules, with use of the pre-defined dictionary[9]. Taking into account the numerous semi systematic fragments retained by IUPAC (e.g., acetic acid instead of systematic ethanoic acid) a only functioning parser will have to work with an extremely large dictionary of morphemes. Once a valid name (the problem of allowed valid names has been already mentioned above) has been successfully parsed, appropriate routines are to be invoked in order to process semantic information as each syntax rule is obeyed. The morphemes localized in the name are then associated with corresponding structural fragments stored in a compact form as small connection tables. These are then combined and ordered together into the final complete connection table (CT) corresponding to the complete name. Graphical routines transform the connection tables into structural diagrams and deliver them as output on terminals or in printed form[10].

Conversions of the sort outlined above have a long tradition. The first use of computerized grammar analysis process, with very limited dictionary of nomenclature terms in comparison with the broad range of constructions allowed in the IUPAC nomenclature, was by Elliot.[11] Later, practical operational computer programs based on such procedures were reported by CAS[12], where they were used to validate the CAS index for the CAS Index File. Approximately at the same time Stilwell[13] and later Cooke-Fox et al[14] reported a very interesting grammar-based nomenclature translation for steroid nomenclature. Another system, excluding, however, semi systematic and trivial fragments from the dictionary of morphemes, was reported by Carpenter[15]. The most advanced research to date of the grammar based translation of IUPAC nomenclature into structural diagrams has been conducted by the team at the University of Hull[2,9-10,14,16-17].

The first functioning practical system translating names into structures (called VICA) dates back to 1986 and was developed by Domokos and Goebels for the IBM mainframe computer in the Beilstein Institute in Frankfurt/Main, Germany. It had been successfully applied in Beilstein (reaching a success rate up to 95%) for Beilstein nomenclature only and was never used outside Beilstein. Except for internal Beilstein memos and technical documents, there are no reviewed publications to which one might refer. The format of the input chemical name accepted by VICA (written in Pascal and Fortran programing language) was strictly defined for the syntax of the systematic nomenclature as used in the "Beilstein dialect" (specific delimiters, specific handling of post-suffixes such as esters and amides, specific syntax of multi-component structures, etc.).

Another interesting attempt in the area of algorithmic name conversion is ROXY, a system designed and programmed in 1993 by Lawson.[18] This Visual Basic program works with a very small dictionary (approximately 500 entries) of pre-defined name fragments, very successfully generates fused and annelated ring system connection tables using strictly algorithmic mechanism (without database lookup) and reaches, for real-life names, a success rate up to 21%.

Recently a few interesting practical (and commercially available) computer systems translating nomenclature into connection tables were released. The first one comes from CambridgeSoft Corporation, Cambridge, Mass., USA and is known under the name "Name=Stru". Its latest version is included in the structure editing package ChemDraw Ultra and the chemical office suite ChemOffice Ultra.[19] The success rate (ratio of correctly generated structures of the total number of structures in the test sample) as reported by Brecher in his paper[20] varied from as high as 92% to as low as 33.5% depending on the quality of names in the source test sample.

The "Name=Stru" system has a few limitations. Cahn-Ingold-Prelog (CIP) stereochemistry (R/S, E/Z) is not supported, and some classes of bridged ring systems are neglected. The system is unable to handle names of polymers and those of inorganic coordination complexes. Also the subtractive nomenclature (de-, des-etc.) stays fully unsupported.

The paper by Brecher includes a detailed description and classification of problems encountered by anyone attempting to design an automatic nomenclature converter. These problems—according to Brecher—arise mainly from the ambiguity of current nomenclature practices.

Advanced Chemistry Development released another program of this type. (ACD Labs, Toronto, Canada). This program is able to exceed in many cases the success rate of the "Name=Stru" program. "ACD/Name to Structure" is offered as an interactive or a batch version (a conversion session can be launched not for a single name, but for a file of input names). The program is claimed by ACD Labs[21] to be able to generate chemical structures for names of most classes of general organic compounds, many derivatives of more than 150 basic natural product parent structures, and semi systematic and trivial names of common organic compounds.

The batch version of the name converter from ACD Labs ("Name to Structure Batch") generates structures from systematic and non-systematic chemical names of general organic, some biochemical, and some inorganic compounds. The input for this program can be native, ACD ChemFolder *.cfd format files, regular ASCII text files, or MDL *.db or *.sdf files. Recently, the functionality of the program was extended and Name to Structure Batch can also convert SMILES strings directly into chemical structures. The program is also available for UNIX platforms. This is particularly important since most of the intranet systems for small-scale chemical databases run on UNIX mini-computers.

Yet another name-to-structure converter comes from ChemInnovation Software, Inc., a company based in San Diego, Calif. The program is named NameExpert. The program is more academic than practical (mainly due to an unacceptably low success rate).[22] The program understands strict systematic IUPAC organic nomenclature. For an input IUPAC chemical name, it creates the corresponding structure in one of three styles: shorthand, Kekule, or semi structural formula. In addition, it can add labels to appropriate atoms and groups. The newest version now supports limited stereochemistry, and includes 8000 drug names and structures.

To make the list of available name-to-structure software packages more complete yet another program must be mentioned, namely IUPAC DrawIt released by Bio-Rad Laboratories Corporate, Hercules, Calif., USA. It cannot be considered in any circumstances as a nomenclature tool for practical corporate use.[23] The main restriction is the maximum number of heavy atoms allowed in the resulting output structure, which is set to 10. The program is relatively effective for strictly systematic IUPAC names, but for common nomenclature like that found in today's literature, the program can offer no more than a single digit success rate. Thus it can be under no circumstances considered as any alternative or competition for Name=Stru or for ACD/Name to Structure.

Chemical nomenclature, and organic nomenclature in particular, published in the literature (journals, patents, technical documentations, etc.) is generally of poor quality. Published rules (e.g., IUPAC) are commonly ignored, misinterpreted, corrupted or extended at will. The nomenclature which today is regarded as "systematic" is defined by the consensus of users' opinions. A "correct name" does not exist. There are "common sense" naming practices e.g., those confined within the Beilstein or CAS "dialects".

Previous software for extracting information from text often produced unacceptable results in terms of accuracy and comprehensiveness. In order to produce extractions with acceptable accuracy and comprehensiveness, a human indexer would be used. However, the use of a human indexer is time consuming and expensive.

SUMMARY

A preferred embodiment of the invention comprises software developed to automatically extract chemical data from documents. This preferred embodiment is focused but not limited to identification and extraction of chemical structures, reactions, and some common physical values from patents.

The core of the software preferably is built on a commercial product (for example, "INSIGHT DISCOVERER™ Extractor" (IDE) from Temis GmbH; see www dot temis-group dot com) that uses standard information extraction technology. Whereas previous technology typically achieved recall and precision values of about 60%, preferred embodiments of the invention get better results by combining chemical knowledge, text mining methods, and linguistic knowledge with intelligent pre- and post-processing, including, in at least some embodiments, plausibility checkers. Exemplary results include values of around 70% for recall and greater than 90% for precision (see below).

"Precision" and "recall" are common measures for the success of information extraction programs. "Recall" relates to quantity and is defined as the proportion of those reactions correctly identified by the software compared to all reactions identified by a human reader (correctly identified reactions/all reactions). "Precision" gives a measurement of the quality of the results and is defined as the proportion of those reactions correctly identified by the software compared to all reactions identified by the software (correctly identified reactions/all identified reactions).

One goal of a preferred embodiment is to extract chemical information from documents and store this information in a database, thus automatically creating an index to the underlying documents. Important search terms for chemists are chemical structures in vector graphic form (connection table). Thus, chemical names found in a document (e.g., a patent) are subjected to a name-to-structure translation.

Another goal is to keep the quality of the data as high as possible, and to keep the error rate at a level comparable to that created by a human indexer.

Among the objects a preferred embodiment can identify are: (1) bibliographic data; (2) chemical names; (3) chemical reaction schemata; and (4) physical data associated to compounds. Preferred architecture is based on external rules (concepts). This makes it easy to expand the scope to other objects, as will be recognized by those skilled in the art. The identified objects and data are extracted from a document and loaded into a database.

Preferred embodiments of the present invention comprise methods and software for processing text documents and extracting chemical data therein. Preferred method embodiments comprise: (a) identifying and tagging one or more chemical compounds within a text document; (b) identifying and tagging physical properties related to one or more of those compounds; (c) translating one or more of those compounds into a chemical structure; (d) identifying and tagging one or more chemical reaction descriptions within the text document; and (e) extracting at least some of the tagged information and storing it in a database.

Another embodiment comprises identifying a yield of product within a reaction. Another comprises translating extracted tagged information into a format convenient for storing in a database. A further embodiment comprises identifying and tagging atomistic properties within a text document; optionally, the atomistic properties comprise one or more of: molecular formulas, numbers, ranges of numbers, physical values, labels, and references within text.

In one embodiment, the text document is an XML-type document; in others, the text document is not an XML-type document, and the method comprises analyzing text based on line breaks, numbering schemes, and special keywords.

In various other embodiments, at least some of the chemical compounds are described by their names; at least some of the chemical compounds are described by molecular formulas; and the chemical structure is represented by a connection table. In a further embodiment, a step of identifying and tagging one or more chemical compounds within a text document comprises comparison to a dictionary of chemical name fragments. In another embodiment, the method comprises identifying and tagging a specific rule selected from a set of pre-defined rules for an identified and tagged compound within an identified and tagged reaction; optionally, rules are defined in terms of concepts. Rules may comprise: starting material, reagent, solvent, catalyst, and product.

BRIEF DESCRIPTION OF THE DRAWINGS

FIG. 3 shows a tagged document where the most relevant tags are identified;

FIG. 4 shows a reaction extracted from a patent;

FIGS. 12-15 show a tagged document in greater detail;

FIG. 17 depicts a representative output of the TEMIS program as described in connection with FIG. 2.

DETAILED DESCRIPTION OF PREFERRED EMBODIMENTS

Chemical names are complex objects composed of name fragments, locants, multipliers, prefixes, suffixes, and brackets. As described in detail below, with the help of a fragment dictionary, Reading Machine (a preferred embodiment of the invention, also referred to herein as "RM") identifies all chemical name fragments in a document. The text environment of each fragment is analyzed to decide which fragments and surrounding locants build a single chemical name. The found chemical names are assigned a tag (namtag).

Figure 1:
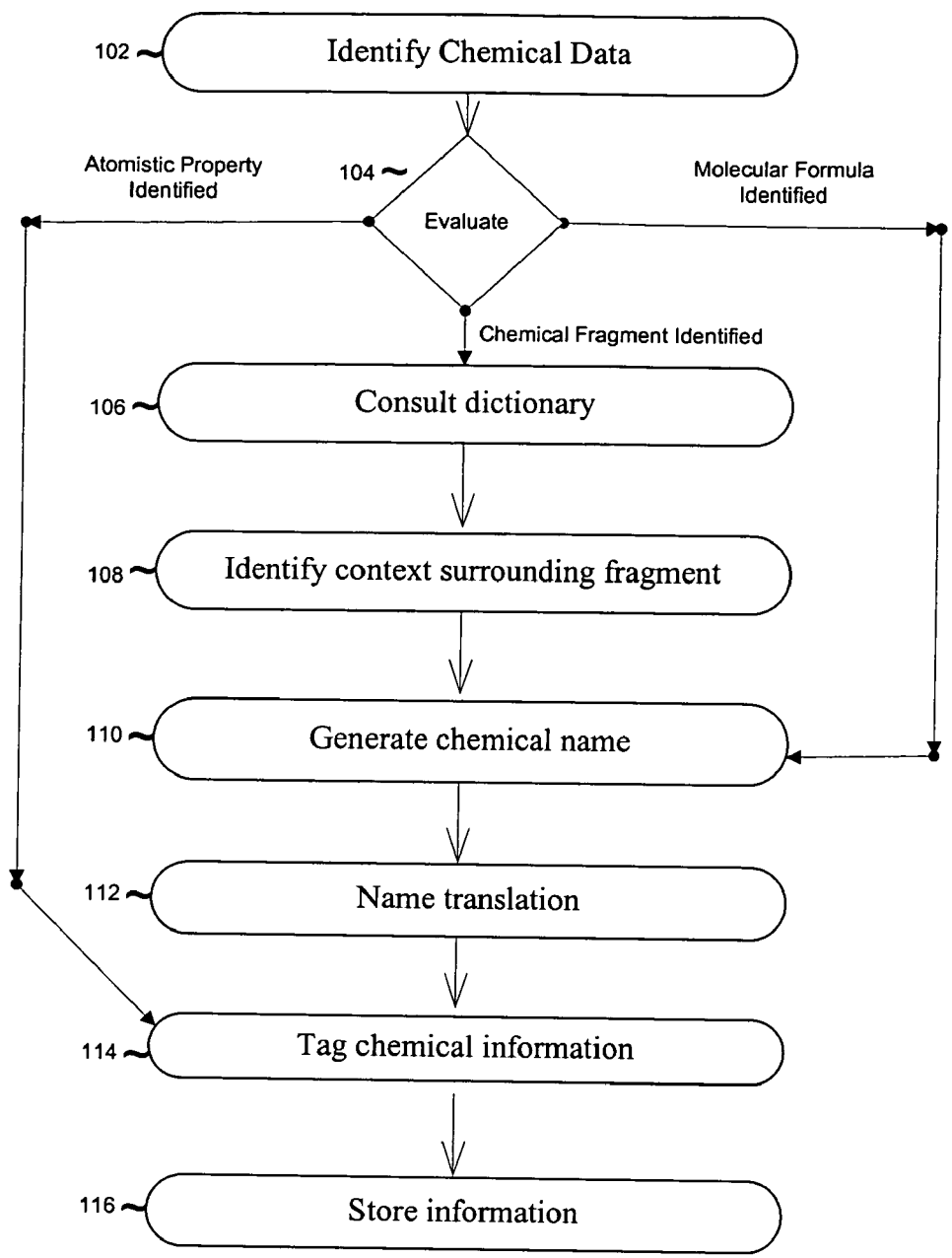
FIG. 1 depicts the workflow of a first preferred embodiment.

FIG. 1 describes the overall data flow of a preferred embodiment.

In step 102, chemical data within the text of a document is identified. Many suitable parsing methods are known in the art, and any one or combination of these may be used to identify chemical data in the text. For example, a database containing a list of chemical fragments can serve as the basis for a data parser.

Chemical data includes chemical structures, chemical fragments, molecular formulas, and "atomistic properties." "Atomistic properties" are those properties that can be tagged without analyzing the context of the chemical data. For example, the following text elements may be atomistic:

Numbers or ranges of numbers

Physical values (numbers plus physical unit), e.g., "mp: 100-120K"

Labels and reference values within the text, e.g., "Example 2a", "3b"

sum formulas

FIG. 12 depicts the identification of a chemical structure in a document. FIG. 13 depicts the identification of physical values in a document. FIG. 14 depicts the identification of chemical names and molecular formulas in a document.

As will be recognized, other chemical data may be identified in the document. For example, acronyms, trivial or trade names, and/or formulas (as described below) may also be identified in a document text. Further, roles of chemical data may be identified (e.g., compounds, proteins, species, diseases, etc.), as well as relationships between chemical data (e.g., product, reagent, binds, inhibits, suppresses, has effect on, is used for, etc.). As will be further recognized, associated data may also be identified for relational database purposes (e.g., company names, inventors, source document(s), or any other desired data).

The identified chemical data is evaluated in step 104, and if a chemical fragment is identified, operation proceeds to step 106. However, if a molecular formula is identified, operation continues to step 110. Further, for identified atomistic properties, and associated data, operation proceeds to step 114.

In step 106, a dictionary is consulted to verify that the identified fragment is correct. In one preferred embodiment, this verification causes operation to proceed to step 108. In other preferred embodiments, syntactic information regarding the fragment is retrieved from the dictionary. This information may further identify the fragment. For example, the information may specify that the fragment can be a name of its own, or that the fragment is allowed only at the beginning/middle/end of a chemical name.

In step 108, the context surrounding the fragment is identified, preferably by identifying those fragments that are connected by a set of allowed characters in a chemical name. Example of potential allowed characters include brackets, numbers, primes, greek letters, single characters, dashes, commas, dots, semicolons, colons, blanks, and words or phrases from a predefined list (e.g., "the salt", "anion", etc.). Combinations of these characters are allowed according to predefined rules. In one preferred embodiment, IUPAC rules are followed (e.g., a single "e" is allowed, but not "ee"). In other embodiments, other standardized rules may be followed. In further embodiments, the rules may be proprietary, or may be created ad hoc.

In one preferred embodiment, when the context of the fragment has been identified, operation proceeds to step 110. However, in other preferred embodiments, the dictionary of step 106 may again be consulted to verify that each fragment, including the surrounding context, is still valid.

Figure 5:
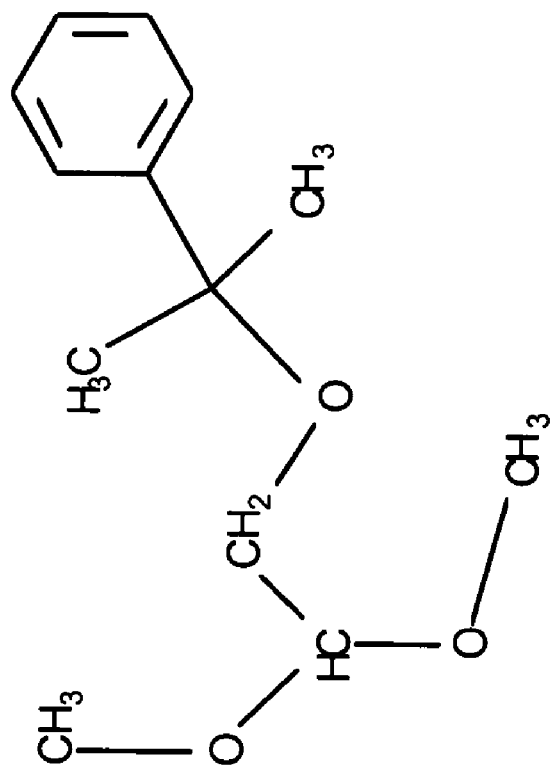
FIG. 5 shows the ambiguity of chemical nomenclature in a chemical structure.

In step 110 the molecular formula or the fragment and surrounding text may be used to generate a chemical name. As described in greater detail below, different naming conventions may yield different names. These naming conventions may be standardized (for example, IUPAC naming), or as known in the art, a name for a structure may accurately describe a structure without properly conforming to any one convention. In one preferred embodiment, only one naming convention is used to generate only one name. In another embodiment, two naming conventions are used to generate two or more chemical names. In yet another embodiment, a combination of naming conventions is utilized to generate a set of names. As described below, despite the existence of a number of conventionally (or unconventionally) generated names for a structure, all of the names may resolve to a unique chemical structure. For example, as illustratively shown in FIGS. 5 and 6, a set of "ambiguous" chemical names represents the same chemical structure.

In step 112, found chemical names generated in step 110 are preferably converted into chemical structures. In a preferred embodiment, the translation of a chemical name into a chemical structure utilizes Reverse Autonom, described in detail below under the section entitled "Reverse Autonom." In another embodiment, translation utilizes a database that contains name to structure relationships (such as Database ACD, a product of MDL Inc, that contains all commercially available chemicals with structures and chemical names; at www dot mdli dot com). In yet another embodiment the program NameToStructure (ACD Labs; at www dot acdlabs dot com) is utilized to convert names to chemical structures. As will be recognized, other programs may be used in this step.

Figure 16:
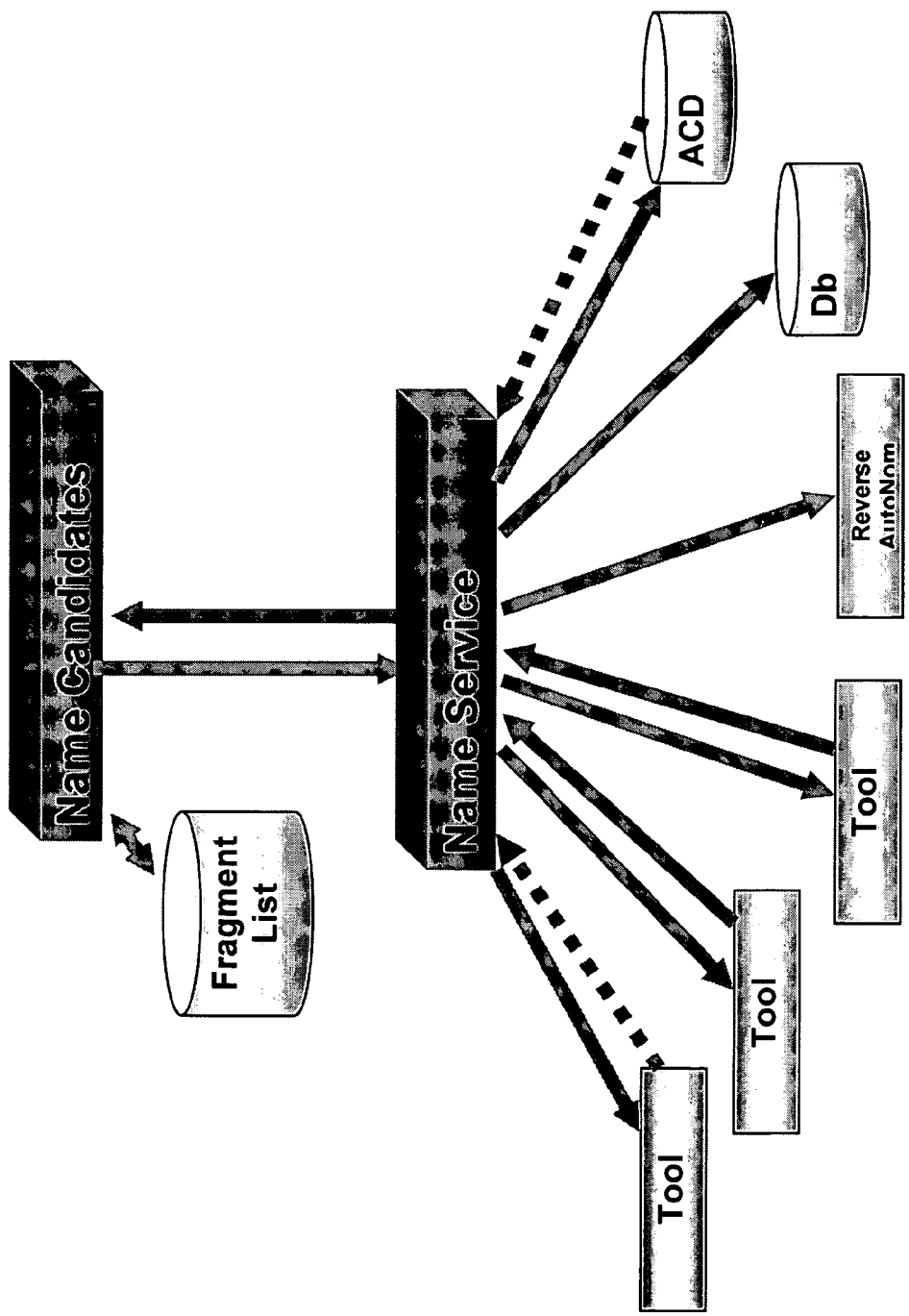
FIG. 16 depicts the workflow of a NameService as described in connection with FIG. 1.

These sources are bundled together to form a "NameService", a service with a SOAP interface which translates chemical names to chemical structures and calculates the coordinates (with the help of the program Cheshire, a product of MDL). An illustrative example of a Nameservice is shown in FIG. 16.

NameService provides: (a) translation to chemical structure via "best source" algorithm; (b) improvement of coordinates; and (c) calculation of metadata (sum formula, unique registration string ("regstring"). The "regstring" a binary string that uniquely identifies a compound. Where means two compounds have identical regstrings, they are identical, and conversely they are not identical if they have different regstrings.

In yet another preferred embodiment, one or more of these sources may be bundled together to form a "NameService". The NameService is preferably a service with a SOAP interface and includes: name to structure translation, coordinate calculation (through the MDL Information Systems program CHESHIRE®—at www dot mdli dot com), and calculation of metadata (e.g., sum formula, unique registration string, etc). As will be recognized, the NameService may include any combination of these functions, or may include other related functionality. Further, the NameService may interface with the RM through any acceptable programmatic means.

In step 114, the found chemical names are tagged in the document. In a preferred embodiment, these tags are in XML format. In other preferred embodiments, these tags are in HTML, SGML, other standardized formats, or proprietary tagging formats.

In step 116, any of the chemical information is stored in a database. For example, in a preferred embodiment, the chemical name and structure are stored in the database. In other preferred embodiments, the metadata, coordinates, chemical names, chemical structures, and/or any other information from steps 102-116 may be stored in the database.

Normalization of Documents

In one preferred embodiment, steps 102-116 of FIG. 1 preferably process documents in XML format. In another preferred embodiment, other formats (e.g., SGML, HTML . . . ) are converted into XML beforehand. In yet another preferred embodiment, the document is processed without any conversion. In yet another preferred embodiment, one format is converted into another format for processing (e.g., optical character recognition text (OCR) is converted into HTML). Where a source document is to be converted, each document type preferably has a document type definition (DTD) file that lists the conversion method. For example, where a document has a formal structure (i.e., a particular document type), a DTD preferably specifies how structures (e.g., tagged structures) in the source document are to be converted. In other instances, where the source document has no formal structure, a DTD may specify that only a root node is to be created containing the whole source text.

Figure 2:
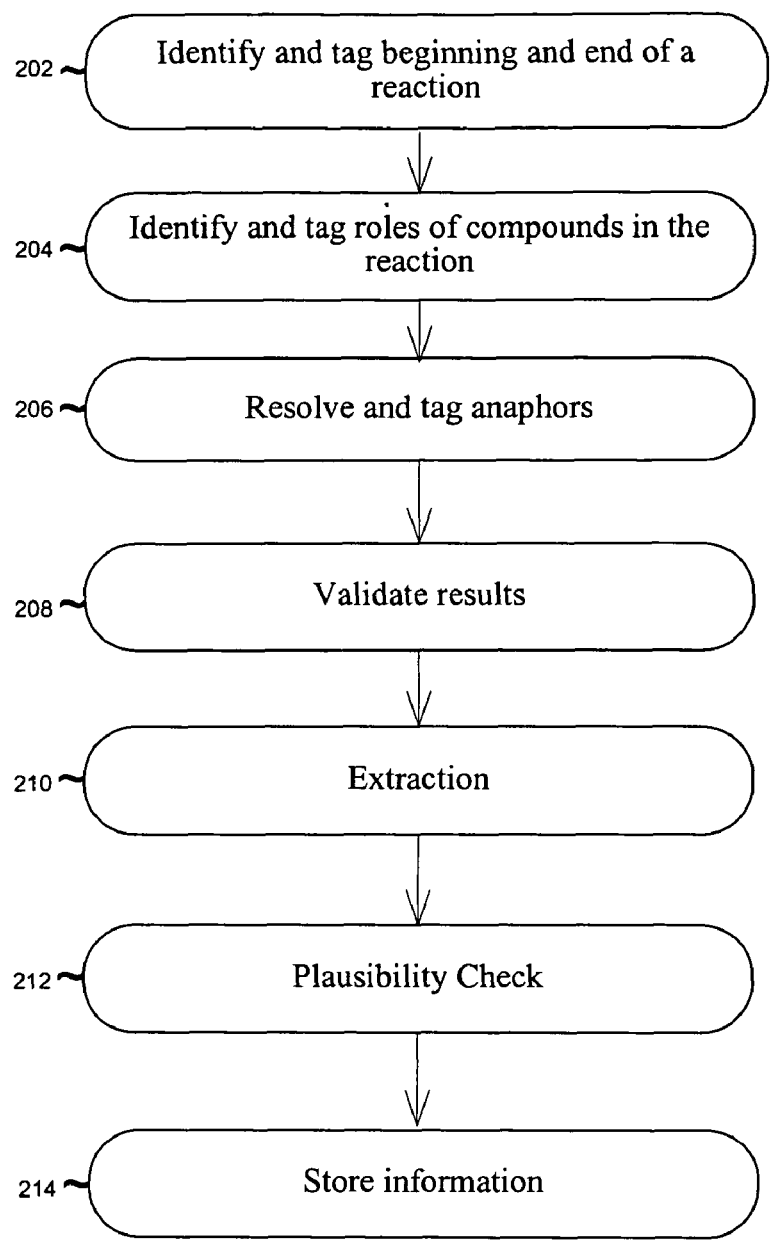
FIG. 2 depicts the workflow of a second preferred embodiment.

FIG. 2 illustrates the workflow of another preferred embodiment.

Reaction Identification

In step 202, chemical reactions are identified within the text of a document. In one preferred embodiment, document structure (e.g., XML or other formal structure) is analyzed to identify the beginning and end of a reaction. In another preferred embodiment, document headers may identify the beginning and end of a reaction. In yet another preferred embodiment, atomistic properties may signify the start and end of a reaction. (e.g., Example 2a). Further, as described above, document normalization may provide structure to determine the chemical reaction start and end. In another preferred embodiment, the beginning and end of a reaction may be created or modified based on the sequence of found and tagged information. For example, a chemical workup section followed by an educt identifies the beginning of a new reaction or a new reaction step.

Role Recognition (Grammar)

The next step (204) is to identify the role of a compound within a reaction. In a preferred embodiment, the role can be: (a) educt (starting material); (b) product; (c) reagent; (d) catalyst; or (e) solvent. The identification of the roles preferably is done utilizing licensed third party programs. One such program is "INSIGHT DISCOVERER™ Extractor" (IDE) from TEMIS. IDE has a built-in library that performs a linguistic analysis of the text (XELDA software from XEROX) and tags the text with the found part of speech for each word (e.g., verb, noun, adjective, etc.) and its basic form. For example, the basic form of the word tested is test. Each word is tagged with this information.

This tagged text is analyzed using "concepts" that are predefined rules expressed as regular expressions. Each concept is a set of lingual similar terms; more basic concepts are combined in more complex concepts. A concept (or pattern) is a rule that defines relationships between words, expressions, or other concepts in a text. If a concept "matches" with text then that piece of text contains the information expressed by that concept. The sense of each sentence is detected by the matching concepts. Text is tagged with its corresponding concept(s). As described in greater detail below, text may be tagged with more than one concept. An illustrative example of tagged text is shown in FIG. 17.

For example, a sentence like "Phenol was mixed with sodium alanate in hexan", is first tagged with names, resulting in "namtag was mixed with namtag in namtag". The proper concept to extract the solvent would be:

```
<concept name="Csolvent" autonomous="TRUE">
    ({REACTANT:namtag})? / in / {SOLVENT:namtag}
</concept>
```

This concept finds a namtag after the word "in" and assigns the role solvent to this namtag. If a namtag is before the "in" this namtag will get the role "reactant." As a further example, the phrase " . . . yielded <namtag>" defines <namtag> as a product.

Rules are defined by analyzing a batch of documents to find all relevant verbs which define a product. For example, Table 1 illustrates some of the various word forms that would define a product.

TABLE 1

| 5604 | Give | give | #VB (verb) |
| 2214 | afford | afford | #VB |
| 1835 | Provide | provide | #VB |
| 1582 | Prepared | prepare | #VBN (participle) |
| 1317 | Obtained | obtain | #VBN |
| 1200 | Gave | give | #VB |
| 640 | Yield | yield | #VB |
| 540 | Afforded | afford | #VBD (past tense) |
| 528 | using | use | #VBG (gerundive) |
| 523 | Reduced | reduce | #VBN |
| 479 | dried | dry | #VBN |
| 440 | Obtain | obtain | #VB |

As further illustrated in Appendix A, a number of "concepts" preferably are defined, where each concept describes one way to express the role of a compound (e.g., educt, product, etc.) As shown in Appendix A, a sequence of the concepts files is defined in the file MDLProdReact.scp. All concepts of level 0 are applied to given text, whereas each concept marks a part of the text. If two marked text fragments overlap, the left-most and longest fragment is used for the further analysis. The same steps are repeated for the next level to a maximum level of 4.

Anaphor Resolution

An "anaphor" is a linguistic pointer to another object. Examples are "the obtained salt" (pointing to the chemical name of the salt), "the product of example 2b" (pointing to the chemical name for the product of the example), "the alcohol was added" (pointing to the chemical name for the alcohol), etc. In step 206, anaphors are tagged as anaphors, as well as being tagged with the chemical name. I.e., the anaphor itself keeps its role as chemical name and the target is determined within the given context. The identification of an anaphor is illustrated in FIG. 15.

Validating Results

The results in a reaction are preferably validated based on a calculated quality level (step 208). In this step, the quality level of the obtained results is compared against some pragmatic parameters (e.g., (a) number of educts; (b) number of products; (c) number of unidentified compounds). Reactions with a quality level below a pragmatically defined threshold are discarded. For example, reactions where no or too many products are found have a low quality level, and are discarded. Where a number of educts results in an acceptable number of products, the reaction may have a high quality level, and would accordingly be accepted.

After this step all relevant objects are tagged in the document. FIG. 3 depicts a tagged reaction where the most relevant tags are visualized.

FIG. 4 illustrates a reaction extracted from a patent and the relevant patent text. As shown in FIG. 4, part 402 represents the extracted data. For example, Product PRN represents the product extracted from the patent text (part 406). Part 404 depicts the associated structure and reaction schema. Part 408 identifies the reference patent used to extract the relevant data.

Extraction

In step 210, (see FIG. 2) found objects are preferably extracted from the document. In one preferred embodiment, the extracted objects are converted into XML format. In another preferred embodiment, the extracted objects are converted into a proprietary format (e.g., PEP-format). As will be recognized, the extracted data may be converted to any desire format (ASCII, Binary, HTML, etc.).

Plausibility Checks

As shown in step 212, the found reactions are checked for their chemical plausibility. This preferably is done by detecting the reaction centers and mapping the atoms of the starting material(s) to the atoms of the product(s). Because all available mapping tools have their strengths and weaknesses, a preferred embodiment uses two or more different tools. For example, "Classify" from InfoChem and "Cheshire", a commercial product of MDL. In this embodiment, reactions that pass 2 of the 3 plausibility checks, for example, are accepted and stored in a database (step 214). In another preferred embodiment, only one of these mapping tools is utilized. In yet another preferred embodiment, any combination of these tools may be used.

In at least one embodiment, a reaction is accepted based on a mapping score. Depending on the percentage of the acceptable mappings, a mapping score may be given by one or more of the above-mentioned tools. When the score passes a threshold level, the reaction is accepted. In this embodiment, special chemical rules may be evaluated to determine the percentage of acceptable mappings (e.g., degree of overlap, reasonable leaving groups, is the level of charge balance reasonable, are the valances of all atoms plausible). Each acceptable mapping has a point value. As will be recognized by those skilled in the art, any combination of these rules, or additional rules, may be used to determine the percentage of acceptable mappings. In these embodiments, if the reaction passes (is plausible) it is stored in a database (step 214). If the reaction does not pass it is rejected. Further, inherently implausible reactions may be rejected (e.g., a reaction may be implausible due to errors in the document (author errors, OCR errors), ambiguous names, misinterpretation of names, or other reasons unrelated to the reaction itself.

In one embodiment, if the reaction does not pass, a second plausibility check using a different embodiment may be attempted. As will be recognized, any combination of the above mapping tools, or additional mapping tools, may be used to verify chemical plausibility. As will be further recognized, any combination of the above embodiments may be used to verify the plausibility check.

Modularity

Figure 11:
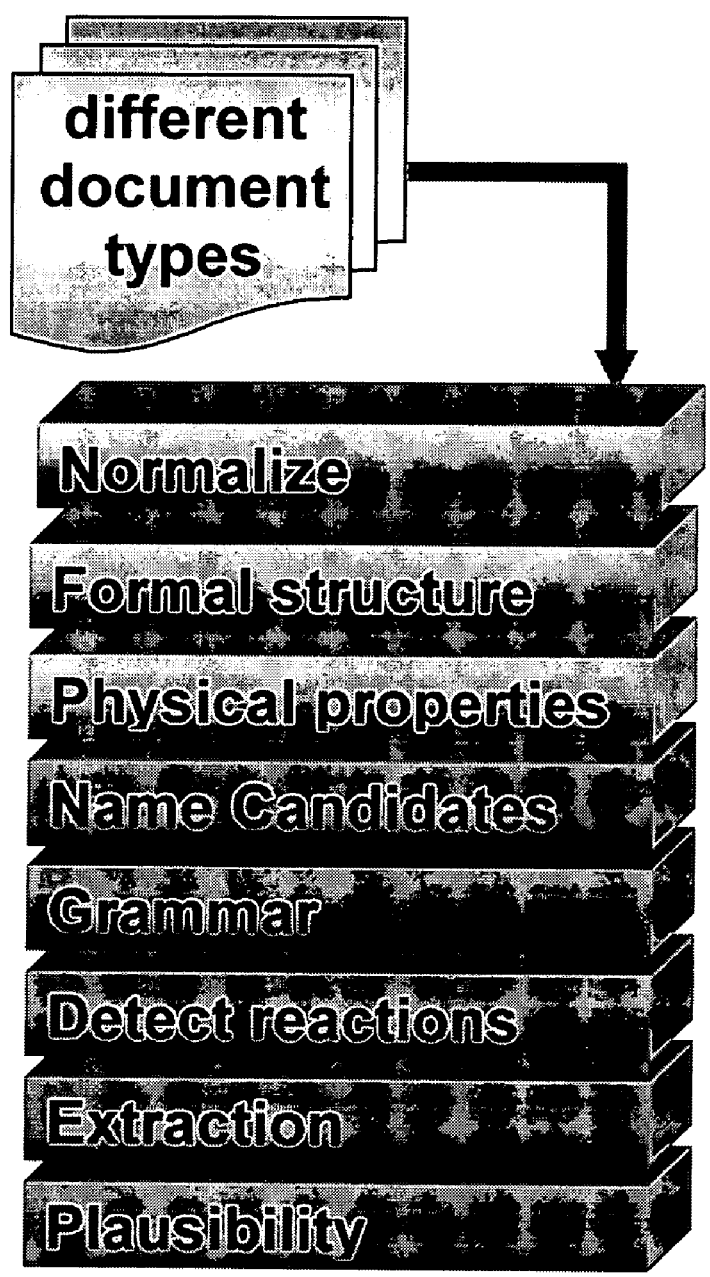
FIG. 11 shows the modularity of a preferred embodiment.

In a preferred embodiment, the software is constructed of modules, where each module is operative to perform one or more steps (see FIG. 11). The benefit of such modularity will be appreciated by those skilled in the art.

Results

Table 2 below illustrates the recall and precision rates of RM. At least 10,000 patents were processed and then a manual Quality Assurance on some thousand reactions was performed.

TABLE 2

| Step | recall | precision |
| --- | --- | --- |
| Chemical names | >95% | >95% |
| reaction identification | >80% | >80% |
| Name to structure | 65% | >98% |

More than 80% of all reactions have been found with correct educts and products. The translation of names to structures is the biggest bottleneck; nevertheless about 50% of all reactions have structures assigned and are of good quality.

Technical Details

Table 3 indicates technical details of a RM. Further preferred embodiments may be created by adding or removing elements. Further, any number of elements from Table 3 may be combined to form additional embodiments. For example, in one embodiment, RM may support only the Microsoft WINDOWS® operating system. In another embodiment, RM may support both WINDOWS® and IBM's AIX. It will be recognized by those skilled in the art that Table 3 provides for a number of preferred embodiments based on the combination of elements. It will be further recognized by those skilled in the art that other operating systems, operating modes, supported input or output formats, and embedded products may be utilized, and those listed in Table 3 are an illustrative list rather than a comprehensive one.

TABLE 3

| | |
| --- | --- |
| Supported Operating systems | Windows, AIX |
| Operating mode | Batch, list of filenames |
| Supported Input formats | XML, SGML |
| Output formats | HTML, XML, SSF |
| Embedded licensed products | IDE from TEMIS, NameToStructure from ACD/Labs. |

Reverse Autonom

The Reverse AutoNom computer program does not rely on the concept of a so called "correct name". As one skilled in the art will recognize, Reverse Autonom algorithms may expect the "worst case scenarios" as far as syntax and used semantics of the input names are concerned. It should be assumed that anything as "systematic nomenclature" is only a vague statement of academics and is not followed in practice.

Reverse AutoNom assumes that so called systematic names are rare and thus Reverse Autonom does its best to convert any name presented as input.

General Design

Although the name "Reverse AutoNom" refers to "AutoNom," the two programs have actually very little in common. The AutoNom (from Automatic Nomenclature) nomenclature generator was the first pioneering program in the area of computer-assisted organic nomenclature translating structure diagrams directly into chemical names[24-28]. The use of term "AutoNom" preceded by "Reverse" is only descriptive and was chosen to indicate to a potential user which conversion she/he can expect from the program.

In a name-to-structure translation, the ambiguous and to a large extent undefined or fuzzy input is the name with all its possible "dialects," allowed notations and vague syntax. Output—the structural diagram—is on the other hand absolutely unique and defined to the smallest details.

The Reverse AutoNom program was designed by taking linguistics of the common usage names into account. The "common usage" is well known in the art. As a basis for quality analysis, over 8 million published names from European, American, and Japanese patent publications from years 1980-2000 were browsed to produce a random sample of 1130 names, which then were manually analyzed by a chemical nomenclature specialist. The following results were obtained:

TABLE 4

Quality of names for a sample of 1130 names extracted on a random basis from patent publications appeared from years 1980-2000

| Quality rate description | % of Names |
| --- | --- |
| IUPAC conformed: no stereochemical symbols in name | 34.10 |
| IUPAC and fully AutoNom conformed | 0.07 |
| IUPAC conformed: stereo symbols present and trivial parts present | 19.90 |
| Conditionally IUPAC conformed, trivial parts present, stereo symbols present (only conditionally convertible) | 13.60 |
| No IUPAC conformed (rather only conditionally convertible) | 6.60 |
| Syntax errors in name, formal or logical errors in name (only conditionally convertible) | 16.40 |
| Non-convertible names (conform to no rules) | 9.30 |
| Names with missing no default locants (rather non-convertible) | 0.03 |

The above statistics were then augmented by the AutoNom's performance[7] results measured for a sample of over 63,000 structures randomly chosen from the Beilstein database for the newest release of the program (AutoNom 2000 and AutoNom TT). Having both these data available made it possible to formulate a set of relevant guidelines, which should be followed if a name-to-structure algorithm could be, to a reasonable extent, successful:

1) IUPAC Rules or Recommendation are Usually Ignored, Violated, or Broken.

Figure 6:
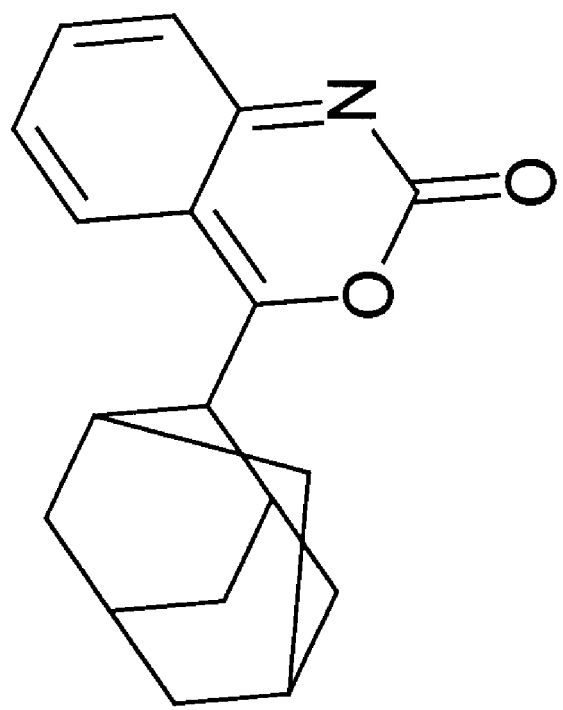
FIG. 6 shows nomenclature styles used for naming chemical structures.

The assumption that the chemical community knows "The Rules" is wrong. Most chemists, if at all, try to conform to either CAS or Beilstein nomenclature systems. Very frequently they mix them together in a single name. Adamantane (retained by IUPAC-forbidden by CAS-allowed by Beilstein) ring name as equivalent to systematic von Baeyer name tricyclo[3.3.1.1$^{3,7}$]decane very often occurs as fragment in a single name together with other fragments such as 3,1-benzoxazine (allowed by IUPAC-forbidden by Beilstein-allowed by CAS). As shown in FIG. 6, alternative names (for the same structure) were encountered in the test sample.

Reverse AutoNom converts each of the names from FIG. 6 into the correct structure.

2) IUPAC Rules or Recommendation are Usually Extended at Will

The name "2-(2,2-diphenylethylamino)-1,4,5,6,7-pentahydro-1,3-diazepine hydrochloride" was found in one of the tested samples. For some nomenclature specialists this name might be shocking. This is obviously a very incorrect name. Odd number of "hydro" prefixes (pentahydro) is strictly forbidden in all nomenclature systems or practices. The number must be even (tetrahydro) and an additional indicated hydrogen prefix (1H) should be used. On the other hand, for the author of this name this rule is probably unknown or too limited and she/he sees nothing wrong in its extension. Both chemist and computer program can convert it with ease into the correct structure. Such an approach to "The Rules" is very widespread in the chemical community.

There is nothing wrong (for chemists) to allow unlimited substitution on carbons in trivial names (retained by IUPAC) such as myristic, stearic or lauric acids (IUPAC and CAS allows it only on the two carbon acetic acid). Acetone is allowed by IUPAC, but trivial names such as butyrone, valerone, stearone, etc. for longer ketones are forbidden (CAS and Beilstein follow IUPAC in this case). For chemists the "ketone rule" of acetone is freely extended for other ketones.

Similarly the established Hantzsch-Widman system for naming of monocyclic rings with heteroatom replacements seems to be extended at will. The latest pre-defined IUPAC list[29] of allowed 19 (The Blue Book from 1979 specifies a list of 22 atoms[6]) heteroatoms for such replacements seems to set no obligation for chemists. If 1,3-oxathiolane is allowed why then 1,3-oxapolonale shouldn't? There is nothing strange in this arbitrary approach, taking into account that even Beilstein and CAS only partially conform to this IUPAC recommendation. Beilstein uses the original extended list of 22 atoms, while CAS use only 14 atoms from the 19-atom list removing all halides and mercury.

Another example of a rather strange interpretation of IUPAC rules is illustrated by the name "1,4-dihydrobenzene" encountered in one of the test samples. The use of the "hydro" prefix to denote added hydrogen atoms (additive nomenclature) is absolutely forbidden for benzene ring. IUPAC recommends the use of subtractive nomenclature ("-ene" and "yne") over cycloalkanes. In this particular case the correct name is "cyclohexa-1,3-diene. On the other hand there is no information missing in the exotic name "1,4-dihydrobenzene" so the name gets converted by the Reverse AutoNom program into the correct structure.

3) Ambiguity in Names is Common and can Only be Solved by Empirical Methods.

The published names are ambiguous and one has to live with it. On the other hand, by detailed and often very strenuous analysis of common usage (upon condition that one has access to statistically representative samples of modern nomenclature) it is possible to determine a kind of logic in the ambiguity of names.

The first phase of the Reverse AutoNom project concentrated exclusively on such an analysis (see Table 4). Names from journals and from high quality databases (e.g., the Beilstein file) were generally ignored since the expected editorial intervention by definition had reduced the frequency of ambiguity. Instead we selected a sample of over 8 million names from European, American, and Japanese patent publications from years 1980-2000. They were extracted from the source patent reports by scanning the paper hard-copy documents and using OCR (Optical Character Recognition) in order to compile an input for further complex computer-based processing by a dedicated program called the Reading Machine. The output from the Reading Machine delivered, among others, the character strings of all chemical names encountered in the source documents. Having retrieved the sample, one could analyse the names and formulate the principles of the common usage for the Reverse AutoNom project.

Figure 7:
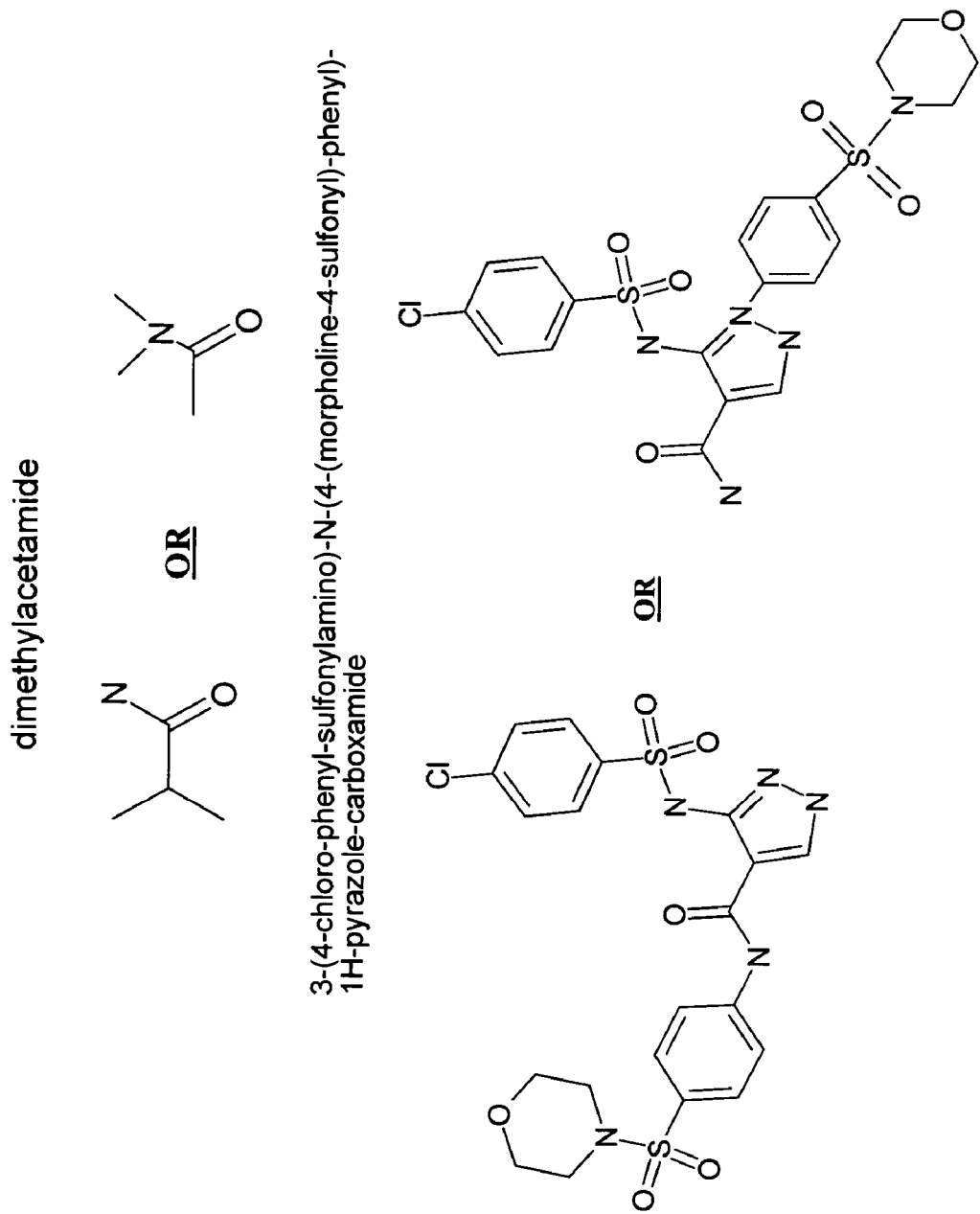
FIG. 7 shows ambiguity of chemical names clarified by empirical analysis common usage.

To illustrate the problem of ambiguity one can consider two simple names (as shown in FIG. 7). In the case of "dimethylacetamide" the default locant for multiplied methyl can be either the nitrogen of the amide post-suffix or the carbon at position 2 of the ethane chain in the "acet" part. Common usage principle points at nitrogen on amide in most of the cases.

In the latter case of pyrazole with carboxamide suffix there are two choices for interpretation of the nitrogen locant "N" in the name: either as position on amide or on the lowest possible N on pyrazole. Common usage analysis shows that the amide nitrogen atom is usually preferred.

Even the most general inspection of chemical names as they are actually published in the documents shows that they need a "lexographical lift." Punctuation and capitalization occurs in all possible varieties. Spacing (important for recognition of multicomponent names) and other delimiters (important, e.g., for esters, ethers, or anions) are fully misused. The names like "4-acetyl-2-(6-oxo-pentadecyl)-phenoxazine-10-carboxylicacid ethylester" are as common as their even worse equivalents "4-acetyl-2-(6-oxo-pentadecyl)-phenoxazine-10-carboxylic-acid-ethyl-ester" which are meant to be the same.

Having set the above principles a preferred embodiment of the Reverse AutoNom was designed. The algorithm preferably executes the following steps:
  lexographical handling (and automatic correction) of the input name;
  name splitting and parsing;
  interpretation of recognized fragments: stem, suffixes, prefixes, infixes, and post-suffixes;
  fragment ordering into so called levels of the name; and
  fragment name assembly
(discussed in greater detail below).

During the first four phases a preferred embodiment of the algorithm creates and identifies objects as well as establishes mutual relations among them. They then are appropriately ordered and compiled into the complete structure during the last phase of the conversion.

In the first prototype of the Reverse AutoNom lexographical handling (and automatic correction) of the input name was absent. It was assumed that names could be ambiguous, could contain genuine errors, or be inadequate in their grammar. The latter two would stop the algorithm already in the phase or parsing. The former could be forwarded for handling in the interpretation and ordering steps of the algorithm. However, shortly after the compilation and detailed syntactic analysis of the pilot representative test sample of names extracted from the patent documents, this assumption had to be verified.

The statistics showed that incoming names had a sloppy syntax in particular in the area of punctuation, spacing and capitalization. Most of such names used what the authors believed to be CAS styling, but that in reality had very little to do with standards defined by the ACS Style Guide manual[30].

Names published in the "Beilstein dialect" of nomenclature were of much better quality, but also in this case the guidelines by Beilstein[31] were often ignored or misinterpreted.

The alphabetic ordering of substituents (as stipulated by IUPAC, CAS, and Beilstein) was frequently ignored. Mother language (non-English) of the authors visibly influenced the syntax of the names published and thus, e.g., "sulphonyl", "alkohol", "alfa", or "gama" were often used instead of the correct "sulfonyl", "alcohol", "alpha", and "gamma."

Delimiters (hyphens, commas, semicolons, full stops, etc.) were used inconsistently. Hydrocarbon ring assemblies, bridged hydrocarbons (von Baeyer systems) and spiro hydrocarbons classes are the here the best examples. The extreme cases include: "<1-1'><3'-1">-ter-cyclo-octane" for the correct (IUPAC/CAS) "1,1';3',1"-tercyclooctane (or [1,1';3',1"] tercyclooctyl by Beilstein), "tricyclo(5,4,0,0-2_9)-undecane" for the correct "tricyclo[5,4,0,0$^{2,9}$]undecane" (commas instead of full stops, hyphen and underline character in the secondary bridge specification instead of superscripts and comma).

Figure 8:
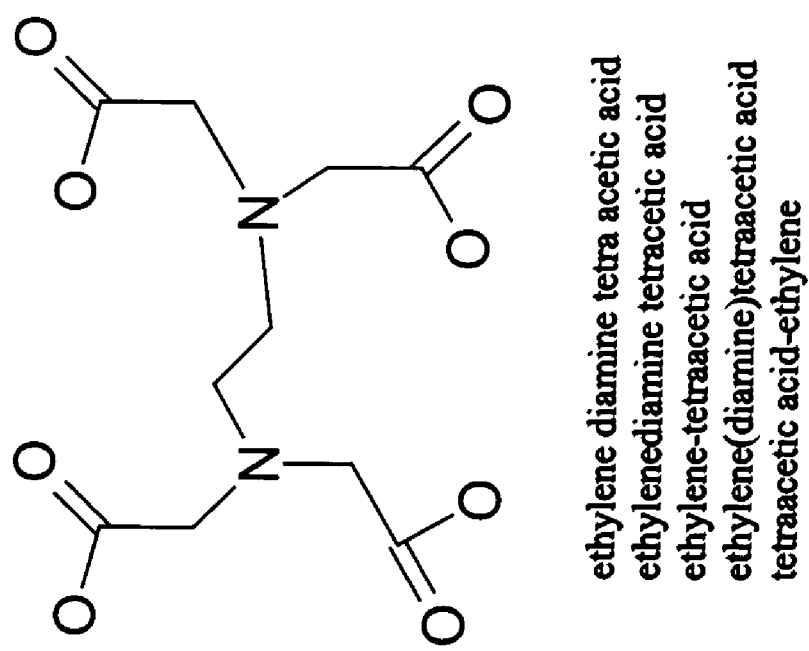
FIG. 8 shows inconsistent use of spacing in nomenclature.

Space as the hard delimiter is extremely important in nomenclature. Fragments on either side of such a space can be interpreted as two components (disjuncted) of the same structure only when the space is determined to be used correctly. Usually it is impossible to make such a statement before completion of interpretation and ordering of fragment in name parts on both of such a space character. To illustrate the problem, it is interesting is to note, that for a single structure (as shown in FIG. 8) none of the 5 names located in the test sample were correct.

As a result of inspection of the input names it was noticed that inclusion into the algorithm as the first step of an intelligent lexographical pre-processor improves the quality of names (obviously without changing their meaning) to such an extent that the estimated success rate would increase by as much as 4.5 and 7.8% for two random samples of approximately 6,500 names in each. Such a pre-processor was programmed and implemented. It contains altogether 10 various routines adjusting names before sending them for parsing and splitting executed in the subsequent step of the algorithm. It eliminates, already in this early stage of the processing, the names which definitely do not conform to the pre-defined standards of the Reverse AutoNom program.

The lexographical pre-processor contains also a dedicated routine that sets global variables (and collects corresponding information data) on the occurrence of such characteristics of the input name as presence of functional but non-CT fragments such as esters, amides, or oximes.

Another important routine examines an input name and strips the explicit stereo descriptors such as e.g. E/Z, R/S, trans/cis, racem, (+/−), etc. off it. One embodiment of the Reverse AutoNom supports stereochemistry only conditionally, i.e., only where it is implicated by the partial names (usually trivial) of potential steric fragments localized in the complete name. Thus a user can expect to receive sterical structures for names containing such fragments as e.g., fumaric acid (E), maleic acid (Z), or nicotine (S), etc. Such structure require stereochemistry interpretation in order to posses any sort of meaning.

The final task executed in the lexographical pre-processing replaces paired parentheses, brackets, and braces ({, [, (, ), ], }) with a unified pair: < for opening and > for closing. They are treated by the algorithm as absolute delimiters and are meant to open and close the sequence of name fragments belonging to a single level. The preferred subsequent steps of the algorithm are then to recursively process all nested levels.

Reverse AutoNom implements simple parsing and splitting. It divides names into recognized fragments of maximum length, starting with the first character and proceeds sequentially. This process is controlled by a table (stored as an ASCII file, or so called Dictionary) containing character strings of chemical terms indexed as morphemes. At this stage the Dictionary contains 34,498 terms carefully selected by the nomenclature specialist at MDL. Each term in the Dictionary is associated with its corresponding short code (also an ASCII string) specifying its functionality. The terms and their codes are loaded into separate tables allocated in the computer memory at the initialisation cycle of the Reverse AutoNom program. Then the algorithm then interrogates (during splitting and parsing) these tables in order to breakdown the input name into recognizable fragments.

This syntax-directed parsing operates by consideration of syntactic classes (locant, separator, substituent, ring, chain, suffix, post-suffix, modifier, etc.) and by the pre-defined hierarchy of these classes. The name units resulting from the parsing are declared to belong to a definite class and each of them receives a "hierarchy stamp" (name parent, prefix for the parent, level stem, prefix for the level stem, suffix, post-suffix, locant, separator within the parent level, modifier within the non-level, etc.). There are no publications describing such a complete hierarchy. For the purpose of the Reverse AutoNom project this hierarchy has been set empirically using, partially, expertise and experience from the past (AutoNom project).

Having established this hierarchy the name splitting and parsing not only breaks a name into fragments, but also relates them immediately to what can be described as "meaning." The parallel table of forementioned codes supplies the meaning. This can be a single integer (as for example to indicate the value of multiplying term, the length of the hydrocarbon chain, or the multiplication factor for a ring assembly, the factor of unsaturation), index pointer to a complete separate connection table (as in case of fused ring systems) or a textual short mnemonics describing the type operation (usually implemented as a single function in the program) that should be executed on the following or preceding fragment (hydrogenation or indicated hydrogen, cyclo, unsaturation, charges, etc.).

In the interpretation and ordering of recognized fragments phase, the complete nomenclature-based interpretation process takes place. Most of the IUPAC/CAS/Beilstein established trivial nomenclature rules, recommendations, and exceptions, which evolved over the years must be considered (and implemented as routines or functions in the conversion program).

Preferably all fragments are interpreted as belonging to one of the following nomenclature class units:
  Stem (parent in the case of the highest "0" level; related to a connection table)
  CT prefix (related to a connection table)
  Function prefix (related to function, e.g., "aza" as the heterocyclic replacement)
  Hydrogenation prefix (e.g., "hydro", indicated H descriptor; related to a forward function)
  Suffix (related to a connection table)
  Post-suffix (e.g., ester, amide, oxime, ion, etc.; related to a function)
  Radical suffix ("-yl", "-ylidene", "-ylidyne"; related to a backward function)
  Unsaturation and saturation descriptor ("-ene", "-yne", "ane-"; related to a backward function)
  Multiplier ("di-", "tri-", "bis-", tris-", "bi-", "tert-", etc.; related to a function)
  Forward function prefix ("cyclo-", "bicyclo[-", "tricyclo[-", "spiro[-", "dispiro[-", etc., related to a function)
  Information container (e.g. "4.4.1.1$^{1,5}$" for secondary bridges specification in von Baeyer systems, or "5.1.7.2" for dispiro subring sizes specification)
  Locant (e.g., "1,2-", "meta", "N-", "C-", "alpha-", "(1)-")
  Stereodescriptor (e.g., "(E)-", "(R)-", "racem.", "alpha-D")
  Separator (hyphen, comma, full point, semicolon, parentheses, brackets, braces, etc.)

The fragments related to a connection table (CT) are rings, chains, or functional groups. The latter are the fragments which are represented in the resulting final structure as acyclic portions of hetero atom arrangements with unsaturated bonds (can also be single hetero atoms as e.g. chalcogens in the alcohols, thioalcohols, etc. The skeletal parts related to the CT fragments are either retrieved directly from a dedicated database accompanying the Reverse AutoNom program or constructed "on the fly" by the algorithm itself. This is for example, the case for all von Baeyer bridged hydrocarbon and heterocycles. The fragment "3,6,8-trioxabicyclo[3.2.2]non-7-yl" is split into:

| | |
|---|---|
| 3,6,8 - | locant |
| tri | multiplier |
| oxa | forward function prefix ("replacement") |
| bicyclo[ | forward function prefix("bicycling") |
| 3.2.2] | information container (secondary bridges specification) |
| non | CT prefix (chain) |
| -7 | locant |
| -yl | radical suffix |

The algorithm preferably locates the core fragment "non" as the main chain (9 carbon atoms), and then using backtracking techniques it works backward to collect the information preceding the chain descriptor. The information container "3.2.2]" directly to the left as well as the forward function prefix "bicyclo[" allow to be sure that the von Baeyer ring system is encountered. Having interpreted this information the algorithm generates (on the fly) the connection table of the bicyclo[3.2.2]nonane ring system. It continues then with the backtracking in order to stop at the locant "3,6,8".

Figure 9:
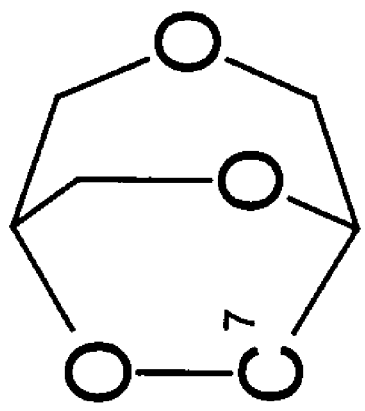
FIG. 9 shows an example of the backtracking and "look forward" operations during interpretation of a localized fragment in a chemical name.

Since the "oxa" forward replacement function is located it is immediately used on the connection table of bicyclo[3.2.2] nonane to exchange the carbons at the positions 3,6, and 8 with oxygen atoms. To conclude the processing of the generated CT the "look forward" routine is invoked. The radical suffix "-yl" is interpreted and locant "-7" is found. The atom at position "7" of the bicyclo[3.2.2]nonane gets stamped with the label "upper connection". The entire fragment "3,6,8-trioxabicyclo[3.2.2]non-7-yl" is thus processed and all its sub-parts are marked as interpreted (as shown in FIG. 9).

After the interpretation, in the following step of the algorithm, all recognized fragments are stamped with a so called level index according to the name level on which they were localized: $[0, 1_0 \ldots N_0]$ for the parent level, $[0, 1, 1_1 \ldots M_1]$ for the highest substituent level directly connected to the parent, $[0, 1, 2, 2_1 \ldots K_2]$ for the next substituent level directly connected to the highest non-parent level, and so on. At the end of the process the input name is fully represented as a tree structure of all the localized name fragments and their mutual relations are recorded in a so called Name Matrix, a multidimensional array of indexes $[0, [1_1, \ldots, M_1], [2_1, \ldots, K_2].]$. This structure is then implemented as a double-linked list of pointers to dynamically allocated and deallocated variant records in a format based on an ordered binary tree[32]. Such an implementation enables the complete mapping of the input name into the final chemical structure once the tree has been fully traversed from the root of the tree to all its leaves.

These two steps, the recognition of fragments and their ordering, constitute the core operations of the Reverse AutoNom algorithm. They were programmed in some 25000 lines of C++ code divided into 88 various functions.

At a preferred fragment name assembly stage of the Reverse AutoNom method the recognized and ordered name fragments have their connection tables assigned (taken from the predefined database or generated algorithmically "on the fly" as, e.g., for hydrocarbon chains) or interpreted (as for multiplier like "penta" or "tert"). The fragments are, at this phase of algorithm, representing complete ligands or core groups. Starting at the highest (root=parent) node of the constructed ordered binary tree representing the input name (and the underlying structure) and traversing the name tree downward, the partial connection tables are consolidated. In order to keep a constant track of the path and the sequential order of the nodes visited while travelling from a given node to the root of the tree (parent CT) the Name Matrix containing the node indexes is accessed. Since the fragments indexed by the Name Matrix are in a strictly sequential order it is possible to program the storage and retrieval of the partial CTs on a "first-in-last-out" stack data structure.

For multicomponent names (usually salts, pseudo-ionic compounds sometimes with big organic substitutions) each component receives its own separate Name Matrix. It is then accessed during the consolidation process and all operations are repeatedly executed (in a recursive manner) for all fragments in this component. Afterwards the complete resulting CT for the component is merged into the CT assembled so far for all previous components.

The fragment name assembly process preferably is, from the very beginning, monitored uninterruptedly by intelligent so-called "illegitimacy" controller routines. The controller (implemented as a collection of over 30 C++ functions) is responsible for the tracking of definite errors, which cannot be resolved within the frames of tolerated ambiguity and/or standard chemistry rules. A typical example of such errors is the explicit collision with valence conventions. Obvious errors in names like "tetrachloroacetic acid" or "fluorocyclopropyne" and less obvious like in "1-(3-methyl-butyl)-4-nitro-1H-pyrrole-2-carboxylicacid[2-(1,4,5,6-tetrahydropyrimidin-3-ylidene)-ethyl]-amide" are rejected by the illegitimacy controller (exceeded valence on nitrogen atom of pyrimidin at the radical suffix position of "-3-ylidene").

In name "1-(3,7,11-trimethyloctyl)azacycloheptan-2-one" the controller will reject the non-existing locant "11" as position for one of the three methyl substitutions on the octyl chain (only eight carbon atoms).

Another case for the controller is the identification of false data delivered by the information container fragments. The two component name "6,8-diazoniadispiro[5.1.6.3]hexadecane dichloride" is rejected after the illegitimacy of the information container prefix "5.1.6.3" (specifying the sizes of terminal rings and the lengths of bridges between both spiro atoms in the three hydrocarbon rings involved in the dispiro junction) is checked against allowed values. The computed value of 17 (5+1+6+3+2) exceeds value of the length of the underlying unbranched-chain hydrocarbon (16, i.e. hexadecane) by one leading to rejection of such a name.

Figure 10:
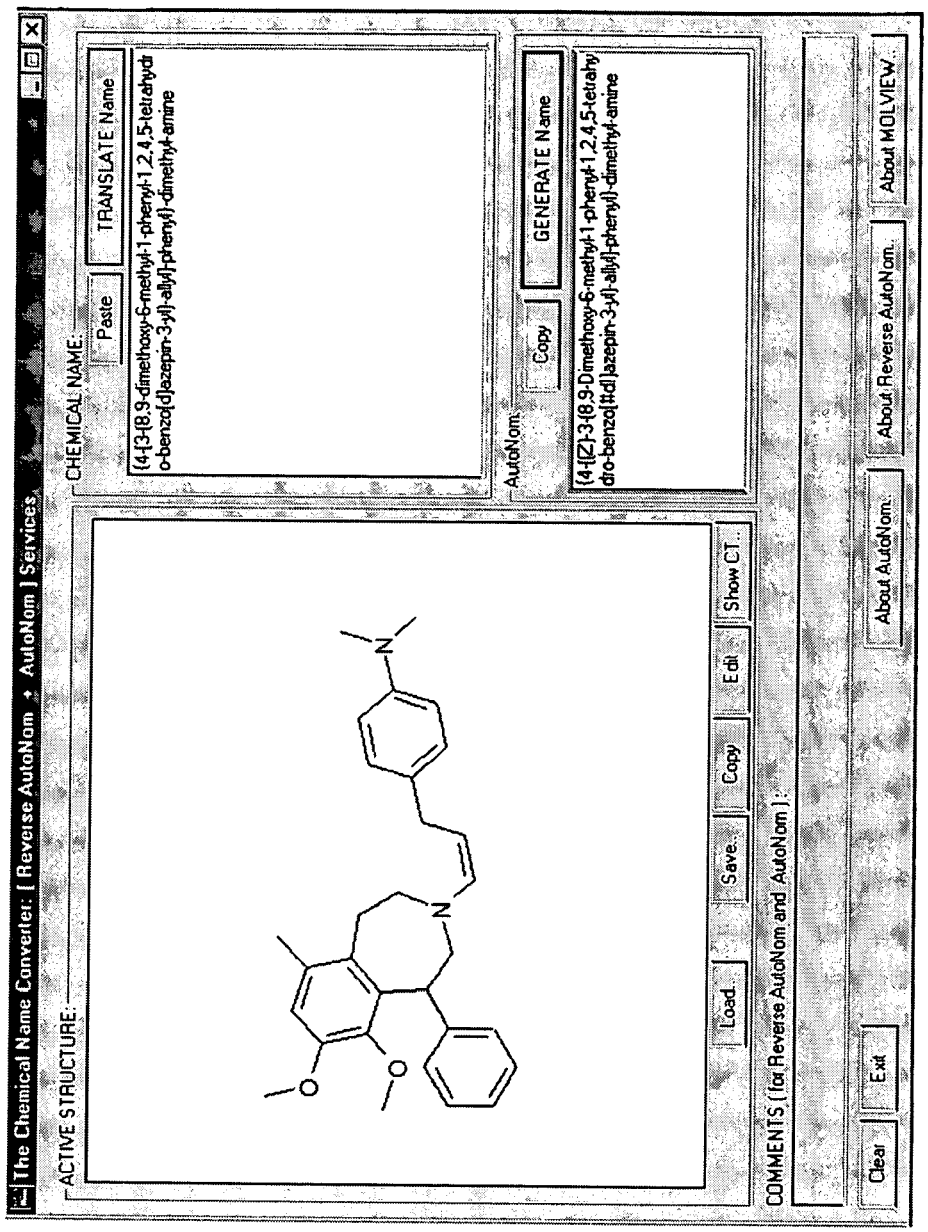
FIG. 10 shows input name and resulting structure from the Reverse AutoNom program.

The process of fragment name assembly ends by merging of all component CTs (if more then one component present) into a single final structure diagram delivered as output from the Reverse AutoNom program. The output is generated as a MOLfile format connection table[32] (approved standard format for structure editors available nowadays in the world) and displayed together with the input name (as shown in FIG. 10).

The program's performance has been measured in various contexts and using test samples representing a very broad spectrum of nomenclature styles used within contemporary nomenclature practices.

At the beginning of the Reverse AutoNom project two so called reference samples were compiled. The first one, given the name "dog food sample" (DF-S), contained a selection of strictly AutoNom names extracted on random from the Beilstein file. The content of the sample of over 1000 names was fixed and never changed during the project. It was demanded that the program (as reversion to its structure-to-name predecessor AutoNom) should, as an absolute minimum, be able to fully converse the systematic computer-generated name; hence the name "dog food." Another reference sample of names, so called "1312 sample" (1312-S) was constructed using names selected at random from journal publications (non-AutoNom ambiguous names, however, with expected editorial quality). These two samples, DF-S and 1312-S were used for test runs as reference (never changed) files at each major upgrade of the Reverse AutoNom program throughout its development. Additionally, it has facilitated the observation and measurement of progress during the course of programming The most comprehensive tests, however, concentrated on the real-life names extracted from the sample of over 8 million entries published in European, American, and Japanese patent reports from years 1980-2000. Their quality was estimated at beginning of the project (see Table 4) and these estimations were then compared with the final statistic data resulting from processing of the whole sample of over 8 million names.

Reverse AutoNom is a success-rate program and it was never expected that it would convert all the names submitted to it as input. Some names simply have no structures associated with them even by the most sophisticated algorithms. Programming a nomenclature converter is possible, but only upon the condition that one takes into account the existing limitations of published nomenclature.

Names that cannot be interpreted by the Reverse AutoNom are grouped into the following general classes:
1. fully unparsable names: there is a group of names, which only in opinion of their authors can be treated as a chemical nomenclature. Names like "D(1)(4)-pregnane-derivative", "#2-RE-Rose Bengal", "D (1)(4)-demethylase enzyme", "D(6)-palmitoyl-acyl-carrier protein composition", or "1,25-dihydroxynated Vitamin D(3)" have meaning only in a very narrow author's context.
2. fully asysematic names: for example here belong names with trivial or catalogue-based nomenclature as well as a huge group of trade names. Names like "linopiridine", "sevin", "carbaryl", "fluctin", or "dyrene" do refer to specific substances; however, the only thinkable solution for their interpretation would be via direct character-to character database retrieval. This approach, in genera, was not considered for the current version of the Reverse AutoNom algorithm.
3. names of natural products
4. macromolecules
5. names of strictly inorganic structures: except for second (or higher) components (as addition to the first, organic, component) represented as inorganic salts, pseudo-ionic, etc.

The tests were run on names "as they come" from the source documents extracted from the sample of over 8 million entries published in European, American, and Japanese patent reports from years 1980-2000. No prior editorial work was done on these names. The entire collection of names was divided into 17 sample text files each of approximately of 500000 names. The following recall (number of output CTs vs. number of input names) was calculated (Table 5):

TABLE 5

Performance of the Reverse AutoNom program as measured for variety of name samples.

| Sample | # of Names | # of CT-s | Recall | Comment |
|---|---|---|---|---|
| DF-S | 912 | 908 | 99.56% | AutoNom names |
| 1312-S | 1312 | 1247 | 95.05% | Journal names |
| 0001.nam | 491200 | 178822 | 36.41% | Patent names |
| 0002.nam | 491227 | 164061 | 33.40% | Patent names |
| 0003.nam | 490436 | 161288 | 32.89% | Patent names |
| 0004.nam | 490356 | 147880 | 30.16% | Patent names |
| 0005.nam | 487728 | 145173 | 29.77% | Patent names |
| 0006.nam | 485972 | 116409 | 23.95% | Patent names |
| 0007.nam | 500000 | 117700 | 23.54% | Patent names |
| 0008.nam | 489932 | 124937 | 23.50% | Patent names |
| 0009.nam | 520047 | 116627 | 22.43% | Patent names |
| 0010.nam | 490375 | 89038 | 18.16% | Patent names |
| 0011.nam | 490460 | 70404 | 14.35% | Patent names |
| 0012.nam | 492419 | 47225 | 9.59% | Patent names |
| 0013.nam | 493002 | 44915 | 9.11% | Patent names |
| 0014.nam | 543190 | 32117 | 5.91% | Patent names |
| 0015.nam | 489233 | 25144 | 5.14% | Patent names |
| 0016.nam | 179334 | 8011 | 4.47% | Patent names |
| 0017.nam | 507076 | 21272 | 4.20% | Patent names |

The results for the first two reference samples (DF-S and 1312-S) are presented here in order to illustrate how much more effective the algorithm could be if the names were strictly unambiguous systematic (DF-S) or at least ambiguously systematic (1312-S). The statistics for samples 0001.nam through 0017.nam are presented in Table 5 in the ascending order of the value of calculated recall. It was, for obvious reasons, not possible to attempt a complete review of all names in the samples, but a cursory examination which confirmed their decreasing quality (more fully unparsable or asystematic names) with the decreasing value of the recall.

More interesting than the recall itself was the analysis of the algorithm's correctness and thus reliability. It could only be examined manually. A random sample of 6182 names was submitted as input to the Reverse AutoNom program. Each of the 1383 resulting output structural diagrams (recall of 22.37%) was then checked against the reference strucural diagram determined to be correct. The number of incorrectly converted names was 10 giving the error rate of 0.72% i.e. relevantly less than one percent.

REFERENCES (1) Garfield, E. Chemico-Linguistics: Computer Translation of Chemical Nomenclature. *Nature* 1961, 192, 196.
(2) Kirby, G. H.; Rayner, J. D. Computer Translation of IUPAC Systematic Organic Nomenclature. 1. Introduction and Background to a Grammar-Based Approach. *J. Chem. Inf. Comput. Sci.* 1989, 29, 101-105.
(3) Cooke-Fox, D. I.; Kirby, G. H.; Rayner, J. D. From Names to Diagrams—by *Computer. Chem. Br.* 1985, 21, 467-471.
(4) International Union of Pure and Applied Chemistry. *Nomenclature of Organic Chemistry, Section A-F and H*, Pergamon, Oxford, U.K., 1979
(5) Smith Jr, H. A. The Centenial of Systematic Organic Nomenclature. *J. Chem. Edu.* 1992, 69, 863-865.
(6) International Union of Pure and Applied Chemistry. "Current projects: IUPAC chemical identifier (IChI), at www dot iupac dot org/divisions/VII/cp8 dot html, (accessed in January 2004).
(7) Wisniewski, J L. Chemical Nomenclature and Structure Representation: Algorithmic Generation and Conversion. In *Handbook of Chemoinformatics: From Data to Knowledge in 4 Volumes*, Gesteiger, J., Ed. Willey-VCH, Weinheim, 2003, Vol. 1, pp 51-79.
(8) Kirby, G. H.; Polton, D. J. Systematic Chemical Nomenclature in the Computer Age. *J. Chem. Inf. Comput. Sci.* 1993, 33, 560-563.
(9) Cooke-Fox, D. I.; Kirby, G. H.; Rayner, J. D. Computer Translation of IUPAC Systematic Organic Nomenclature. 2. Development of a Formal Grammar. *J. Chem. Inf. Comput. Sci.* 1989, 29, 106-112.
(10) Cooke-Fox, D. I.; Kirby, G. H.; Rayner, J. D. Computer Translation of IUPAC Systematic Organic Nomenclature. 4. Concise Connection Tables to Structure Diagrams. *J. Chem. Inf. Comput. Sci.* 1990, 30, 122-127.
(11) Elliot, P. M. *Translation of Chemical Nomenclature by Syntax Controlled Techniques*. Ohio State University, 1969.
(12) Van der Stouw, G. G.; Elliot, P. M.; Isenberg, A. C. Automated Conversion of Chemical Substances Names to Atom Bond Connection tables. *J. Chem. Doc.* 1974, 14, 185-193
(13) Stilwell, R. W. Computer Translation of Systematic Chemical Nomenclature to Structural Formulas—Steroids. *J. Chem. Doc.* 1973, 13, 107-109.
(14) Cooke-Fox, D. I.; Kirby, G. H.; Lord, M. R.; Rayner, J. D. Computer Translation of IUPAC Systematic Organic Nomenclature. 5. Steroid Nomenclature. *J. Chem. Inf. Comput. Sci.* 1990, 30, 128-132.
(15) Carpenter, N. Syntax Directed Translation of Organic Chemical Formulae into Their 2-D Represenataion. *Comput. Chem.* 1975, 1, 25-28.
(16) Cooke-Fox, D. I.; Kirby, G. H.; Rayner, J. D. Computer Translation of IUPAC Systematic Organic Nomenclature. 3. Syntax Analysis and Semantic Processing. *J. Chem. Inf. Comput. Sci.* 1989, 29,112-118.
(17) Cooke-Fox, D. I.; Kirby, G. H.; Rayner, J. D. Computer Translation of IUPAC Systematic Organic Nomenclature. 6. (Semi)Automatic Name Correction. *J. Chem. Inf. Comput. Sci.* 1991, 31, 153-160.
(18) Lawson, A. *Internal communictation*, MDL Information Systems GmbH, Frankfurt am Main, Germany, 2003.
(19) CambridgeSoft Corporation, Cambridge, Mass. USA, at products dot cambridgesoft dot com/ProdInfo dot cfm-?pid=295 (accessed in January 2004).
(20) Brecher, J. Name=Stru: A Practical Approach to the Sorry State of Real-Life Chemical Nomenclature. *J. Chem. Inf. Comput. Sci.* 1999, 39, 943-950.
(21) ACD Labs. Products: ACD/Name, www dot acdlabs dot com/products/name_lab/name/, (accessed in January 2004).
(22) ChemInnovation Software Inc. CA, USA, www dot cheminnovation dot com/products/nameexpert dot asp (accessed in January 2004).
(23) Bio-Rad Laboratories Corporate, Hercules, Calif., USA, www dot chemwindow dot corn (accessed in January 2004).
(24) Wisniewski, J. L. AUTONOM: System for Computer Translation of Structural Diagrams into IUPAC-Compatible Names. 1. General Design. *J. Chem. Inf. Comput. Sci.*, 1990, 30, 324-332.

(25) Goebels, L., Lawson, A. J., Wisniewski, J. L.: AUTONOM: System for Computer Translation of Structural Diagrams into IUPAC-Compatible Names. 2. Nomenclature of Chains and Rings. *J. Chem. Inf. Comput. Sci.,* 1991, 31, 216-225.

(26) Wisniewski, J. L. Autonom—A Chemist's Dream: System for (Micro) Computer Generation of IUPAC-Compatible Names from Structural Input. In *Chemical Structures 2*, Warr, W. A., Ed. Springer-Verlag, Berlin, Heidelberg, 1993, pp 55-63.

(27) Wisniewski, J. L. AutoNom. In *The Beilstein System: Strategies for Effective Searching*, Heller, S. R, Ed. American Chemical Society, Washington, D.C., 1997, pp 161-197.

(28) Wisniewski, J. L. Nomenclature: Automatic Generation and Conversion. In *Encyclopedia of Computational Chemistry*, von Rague Schleyer, P.; Allinger, N. L.; Clark, T.; Gesteiger, J.; Kollman, P. A.; Schaefer III, H. F.; Schreiner, P. R., Eds. John Wiley & Sons Ltd., Chichester, 1998, Vol. 3, pp 188-202.

(29) International Union of Pure and Applied Chemistry. *A Guide to IUPAC Nomenclature of Organic Chemistry, Recommendations* 1993; Panico, R., Powell, W. H., Richer, J. C., Eds.; Blackwell Science, Oxford, U.K., 1993; Recommendations R-2.3.3.1.3; pp 2591-2601.

(30) *The ACS Style Guide: A Manual for Authors and Editors,* $2^{nd}$ ed.; Dodd, J. S., Ed.; American Chemical Society, Washington, D.C., 1997, pp 56-67.

(31) *Prefix List: Beilstein Handbook of Organic Chemistry*, Springer-Verlag, Heidelberg, 1990, pp LV-CXXXV

(32) Hubbard, J. R. *Data Structures with C++*. McGraw-Hill, New York, 2000, pp 174-182.

(33) Dalby, A., Nourse, J. G., Hounshell, W. D., Gushurst, A. K. I., Grier, D. L., Leland, B. A., Laufer, J.: Description of Several Chemical Structure File Formats Used by Computer Programs Developed at Molecular Design Limited. *J. Chem. Inf. Comput. Sci.,* 19921, 32, 244-255.

Appendix A

The concept ~NAME encapsulates different representatives of a compound.
<concept name="~NAME" display="never" autonomous="true">
(~NamTag)+
(~ClassTag)+
(~LabTag)+
(~SufTag)+
(~BezTag)+
</concept>
For instance the concept ~NAME is used in the concept ~TechnicalMention:
<concept name="~TechnicalMention" display="never" level="1">
( (~ValTag|~ComplexValues) / (\%)? / of )? / (the)? / (:desired|crude|crystalline)? / (title)?
/ {PRODUCT: (~NAME)} / (of)? / (#JJ)* / (~ComplexValues)?
be / :charged / with / (~ComplexValues / (\%)? / of)? / ( pure )? / {REACTANT:
(~NAME)} / (of)? / (#JJ)* / (~ComplexValues)?
be / :treated / with / (~ComplexValues / (\%)? / of)? / ( pure )? / {REACTANT:
(~NAME)} / (of)? / (#JJ)* / (~ComplexValues)?
</concept>
... which is part of the concept ~CompoundMention:
<concept name="~CompoundMention" display="whenreferenced" level="1">
~TechnicalMention
~GenericMention
~AnaphoricMention
(~AnaphoricMention|~TechnicalMention) / (~Delimiter /
(~AnaphoricMention|~TechnicalMention))* / (~Delimiter)? / (or|and) /
(AnaphoricMention|~TechnicalMention)
</concept>
The concept ~YieldAct detects the verb yield in its active form:
<concept name="~YieldAct" searchOn="form" display="never" autonomous="true">
to / yield
yield
yielded
yielding
yields
</concept>
All active verbs of a potential product context are clustered to one concept:
<concept name="~ActProductVerbRight" level="1" display="never" autonomous="true">

(~AffordAct|~ConvertIntoAct|~ExtractAct|~ToFormAct|~GiveAct|~IsolateAct|~LeaveAct|
~ObtainAct|~PrecipitateAct|~PrepareAct|~ProduceAct|~ProvideAct|~RecoverAct|~ResultI
nAct|~YieldAct)
</concept>
... resulting in the definition of the compound as product:
<concept name="~CProductAct" level="1" display="always">
~ActProductVerbRight / (ANY|~Interphrase|~WhatReactantOrProductInvis)* /
~CompoundMention
~CompoundMention / ~ActProductVerbLeft </concept>

PRODUCT_Contexts.scp

```xml
<?xml version = '1.0'?>

<!-- sc version = 'V1.20.0009' date = '2003-12-17' -->
<!-- <copyright>(c) copyright 2001, MDL</copyright -->

<component>

<!-- ***************************************** -->

<!-- nouns that are potentially followed by a product -->
<concept name="~ProductNoun" searchOn="form" display="never" autonomous="true">
        <!-- SR, 2003-05-23: "\:" inserted -->
        (#AT)? / (successful|#JJ)* /
(collection|formation|generation|precipitation|preparation|production|result#NN|yield#NN)
/ (\:|of|from)?
        conversion / to
</concept>

<!-- verbs that occur in contexts with a ~ProductionNoun -->
<concept name="~VerbInNominalizationContext" searchOn="form" display="never"
autonomous="true">
        observed
        begins
        starts
</concept>

<!-- ***************************************** -->

<concept name="~AffordAct" display="never" autonomous="true" searchOn="form">
        to / afford
        afforded
        affording
        afford
        affords
</concept>

<concept name="~AffordPass" display="never" autonomous="true">
        (have|#MD)? / be / (#RB|#OD|#WPO)? / afford
</concept>

<concept name="~AffordParticiple" display="never" autonomous="true">
        afforded
</concept>

<!-- ***************************************** -->
<!-- SR, 2003-11-14 -->
```

```xml
<concept name="~Comprising" display="never" autonomous="true" searchOn="form">
    comprising
</concept>

<concept name="~ConvertIntoAct" display="never" autonomous="true">
    convert / (#NN|#RB)? / (into|to)
</concept>

<!-- x was converted from y -->
<concept name="~ConvertFromPass" display="never" autonomous="true">
    (have|#MD)? / be / (#RB|#OD|#WPO)? / convert / from
</concept>

<!-- y was converted into x -->
<concept name="~ConvertIntoPass" display="never" autonomous="true">
    (have|#MD)? / be / (#RB|#OD|#WPO)? / convert / (#NN|#RB)? / (into|to)?
</concept>

<concept name="~ConvertFromParticiple" display="never" autonomous="true"
searchOn="form">
    converted / (from)?
</concept>

<!-- SR, 2003-05-13: new verb -->
<concept name="~CrystallizePass" display="never" autonomous="true"
searchOn="form">
    crystallized|recrystallized
</concept>

<!-- ************************************* -->

<concept name="~ExtractAct" display="never" autonomous="true" searchOn="form">
    to / extract
    extracting
</concept>

<concept name="~ExtractPass" display="never" autonomous="true">
    (have|#MD)? / be / (#RB|#OD|#WPO)? / extract / (from)?
</concept>

<concept name="~ExtractParticiple" display="never" autonomous="true"
searchOn="form">
    extracted / (from)?
</concept>

<!-- ************************************* -->

<concept name="~ToFormAct" searchOn="form" display="never" autonomous="true">
```

```
            to / form
            forming
</concept>

<concept name="~FormAct" searchOn="form" display="never" autonomous="true">
        formed
        forms#VBZ
</concept>

<concept name="~FormPass" display="never" autonomous="true">
        (have|#MD)? / be / (#RB|#OD|#WPO)? / form
</concept>

<concept name="~FormParticiple" searchOn="form" display="never"
autonomous="true">
        formed
</concept>

<!-- ***************************************** -->

<concept name="~GiveAct" searchOn="form" display="never" autonomous="true">
        give
        gave
        gave / IN
        gave / directly
        to / give
        giving
        gives
</concept>

<!-- There is no ~GivePass and no ~GivenParticiple since the word "given" is mostly used
to structure the text and not to mark a product. -->

<!-- ***************************************** -->

<concept name="~IsolateAct" display="never" autonomous="true" searchOn="form">
        to / isolate
        isolating
        isolated
</concept>

<concept name="~IsolatePass" display="never" autonomous="true">
        (have|#MD)? / be / (#RB|#OD|#WPO)? / isolate / (from)?
</concept>

<concept name="~IsolateParticiple" display="never" autonomous="true"
searchOn="form">
        isolated / (from)?
```

```
</concept>

<!-- ****************************************** -->

<concept name="~LeaveAct" display="never" autonomous="true" searchOn="form">
    to / leave
    leaving
    leaves
</concept>

<!-- There is no ~LeavePass and no ~LeaveParticiple since the word "left" is not used in the corpus. -->

<!-- ****************************************** -->

<!-- SR, 2003-03-13: optional comma inserted -->
<concept name="~ObtainPass" display="never" autonomous="true">
    (have|#MD|#CM)? / be / (#RB|#OD|#WPO)? / obtain
</concept>

<concept name="~ObtainAct" display="never" autonomous="true">
    to / obtain
    obtaining
    obtains
</concept>

<concept name="~ObtainParticiple" searchOn="form" display="never" autonomous="true">
    obtained
</concept>

<!-- SR, 2003-03-13/7: specific forms -->
<!-- SR, 2003-05-20: ... more ... -->
<concept name="~ObtainParticipleExample" display="never" autonomous="true">
    <!-- SR, 2003-11-10: "above" more general -->
    ~ObtainParticiple / (as)? / (in|by|(above / under)) / (the|this)? / (above)? / (Example|Stage|Step|way|~IgnLabTag) / (~LabTag)?
    ~ObtainParticiple / as / :described / (( in / Example / (~LabTag)? )|( above ))
    <!-- SR, 2003-06-02 -->
    ~ObtainParticiple / above
    <!-- SR, 2003-08-27: "from the previous reaction" -->
    ~ObtainParticiple / from / ( ~WhatCompanies | ( the / previous / reaction ) )
</concept>

<concept name="~ObtainFrom" display="never" autonomous="true">
    (so)? / (~ObtainPass|~ObtainParticiple) / (from | in | #VBG | be)
</concept>
```

```
<!-- SR, 2003-03-11 ********************** -->
<concept name="~RemainAct" searchOn="form" display="never" autonomous="true">
    remain
    <!-- SR, 2003-05-13: that, which -->
    (that|which)? / remains
</concept>

<!-- ****************************************** -->

<concept name="~RecoverAct" searchOn="form" display="never" autonomous="true">
    recover
    to / recover
    recovered
    recovers
</concept>

<concept name="~RecoverPass" display="never" autonomous="true">
    (have|#MD)? / be / (#RB|#OD|#WPO)? / recover
</concept>

<concept name="~RecoverParticiple" searchOn="form" display="never" autonomous="true">
    recovered
</concept>

<!-- ****************************************** -->

<concept name="~PrecipitateAct" searchOn="form" display="never" autonomous="true">
    to / precipitate
    precipitate#VB / (out)?
    precipitating
    <!-- SR, 2003-12-17 -->
    <!-- precipitates -->
    <!-- precipitated -->
    ( addition / of / ~NamTag )? / precipitates
    ( addition / of / ~NamTag )? / precipitated
</concept>

<concept name="~PrecipitateParticiple" display="never" autonomous="true" searchOn="form">
    precipitated
</concept>

<concept name="~PrecipitatePass" display="never" autonomous="true">
    (have|#MD)? / be / (#RB|#OD|#WPO)? / precipitate#VBN
    :precipitate#VBN
    :precipitate#VB
```

```
            :precipitate#VBD
</concept>

<!-- SR, 2003-11-07 -->
<concept name="~PrecipitateActHide" display="never" autonomous="true"
searchOn="form">
        precipitated / into
</concept>

<!-- ***************************************** -->

<concept name="~PrepareAct" display="never" autonomous="true">
        to / prepare
        it / be / prepare
        preparing
        prepares
</concept>

<concept name="~PrepareParticiple" display="never" autonomous="true"
searchOn="form">
        <!-- SR, 2003-05-13: by; so -->
        (so)? / prepared / (therefrom|from|by)?
</concept>

<!-- SR, 2003-05-13: specific -->
<concept name="~PreparePassReactant" display="never" autonomous="true">
        (have|#MD)? / be / (#RB|#OD|#WPO)? / :prepared / by
</concept>

<concept name="~PreparePass" display="never" autonomous="true">
        (have|#MD)? / be / (#RB|#OD|#WPO)? / prepare / (from)?
</concept>

<!-- SR, 2003-03-21 -->
<concept name="~PrepareParticipleExample" display="always" autonomous="true">
        <!-- SR, 2003-05-20 -->
        <!-- ~PrepareParticiple / ( ( as / :described ) | ( in / stage ) ) -->
        <!-- SR, 2003-06-02: "same manner" -->
        ~PrepareParticiple / (as)? / (in|by|(above / under)) / (the|this)? /
(Example|Stage|Step|way|~IgnLabTag|(same/manner)) / (~LabTag)?
        ~PrepareParticiple / as / :described / (( in / (example|stage|~WhatPatOffices) )|(
above ))
        <!-- SR, 2003-08-27: "from the previous reaction" -->
        ~PrepareParticiple / ( the / previous / reaction )
        <!-- SR, 2003-06-02: specific ... -->
        {REACTANT: ~NAME} / ~PrepareParticiple / :adding / {REACTANT: ~NAME}
        be / :added / {REACTANT: ~NAME} / (solution)? / (in / {SOLVENT:
~NAME})? / ~PrepareParticiple
```

```
         be / :dissolved / in / #AT / solution / of / {REACTANT: ~NAME} / (in /
{SOLVENT: ~NAME})? / ~PrepareParticiple
</concept>
<!-- ***************************************** -->

<concept name="~ProduceAct" display="never" autonomous="true" searchOn="form">
        to / produce
        producing
        produces
</concept>

<concept name="~ProducePass" display="never" autonomous="true">
        (have|#MD)? / be / (#RB|#OD|#WPO)? / produce
</concept>

<concept name="~ProduceParticiple" display="never" autonomous="true"
searchOn="form">
        produced
</concept>

<!-- SR, 2003-03-21 -->
<concept name="~ProduceParticipleExample" display="always" autonomous="true">
        ~ProduceParticiple / :according / to / example
        ~PrepareParticiple / :according / to
        <!-- SR, 2003-11-18: specific -->
        with / {REACTANT: ~NAME} / in / {SOLVENT: ~NAME} / ~ProduceParticiple
</concept>
<!-- ***************************************** -->

<concept name="~ProvideAct" display="never" autonomous="true" searchOn="form">
        to / provide
        provided
        providing
        provides
        provide
</concept>

<concept name="~ProvidePass" display="never" autonomous="true">
        (have|#MD)? / be / (#RB|#OD|#WPO)? / provide / (from)?
</concept>

<concept name="~ProvideParticiple" display="never" autonomous="true"
searchOn="form">
        prodvided
</concept>

<!-- ***************************************** -->
```

```xml
<concept name="~ResultInAct" display="never" autonomous="true" searchOn="form">
    resulting / (in)?
    result / in
    results / in
    resulted / in
</concept>
```

<!-- A passive context for the verb result is not necessary. -->

```xml
<!-- SR, 2003-05-13: new -->
<concept name="~SeparatePass" display="never" autonomous="true">
    be / :separated / by
</concept>

<!-- SR, 2003-05-28: hide substitution -->
<concept name="~SubstituteAct" display="always" autonomous="true">
    (but|except) / :substituting / {REACTANT: ~NAME} / for / {HELPER: (~NamTagAll)}
</concept>

<concept name="~SynthesizePass" display="never" autonomous="true">
    <!-- SR, 2003-05-20: "s" -->
    (have|#MD)? / be / (#RB|#OD|#WPO)? / (synthesize|:synthesised)
</concept>

<concept name="~SynthesizeFrom" display="never" autonomous="true">
    ~SynthesizePass / from
</concept>
<!-- ****************************** -->
<!-- SR, 2003-03-11: excludes the nomen -->
<concept name="~YieldActExclude" searchOn="form" display="never" autonomous="true">
    <!-- SR, 2003-05-14: "from" -->
    ~ValTag / (yield)? / ( ( based / on )|from ) / (:recovered)?
</concept>

<concept name="~YieldAct" searchOn="form" display="never" autonomous="true">
    to / yield
    yield
    yielded
    yielding
    <!-- SR, 2003-12-03 -->
    yields / ( (#CM)? / respectively / (#CM)? )?
</concept>

<concept name="~YieldPass" display="never" autonomous="true">
    (have|#MD)? / be / (#RB|#OD|#WPO)? / yield
</concept>
```

```
<concept name="~YieldParticiple" display="never" autonomous="true"
searchOn="form">
        yielded
</concept>
</component>
```

PRODUCT_CompoundMention.spc

```xml
<?xml version = '1.0'?>

<!-- sc version = 'V1.20.0009' date = '2003-12-17' -->
<!-- copyright>(c) copyright 2001, MDL</copyright -->

<component>

<!-- specifies potential antecedent expressions -->
<concept name="~AnaphoricTerm" display="never" autonomous="true" level="1">
        <!-- AH, 2002-10-31: EX -->
        (ex | Ex | EX) / (\.|\-|\))*
        example
        <!-- AH, 2002-10-31: Example -->
        Example
        formula
        method
        stage
        step
</concept>

<concept name="~AnaphoricMention" display="never" level="1">
        <!-- If it is wanted to extract an anaphoric term alone than the concept
~AnaphoricTerm has to be added here.-->
        ~WHATProdAsAnaphoric
        <!-- EX: the title namtag -->
        {ANAPHORIC_PRODUCT: (title|titled) / ~NAME}
        <!-- EX: the namtag product -->
        <!-- SR, 2003-03-19 -->
        {PRODUCT: ~NAME} / ~WHATProdAsAnaphoric
        <!-- EX: the namtag labtag -->
        ~NAME / {ANAPHORIC_PRODUCT: ~LabTag }
        <!-- EX: the title product of example labtag -->
        <!-- EX: the compounds of example labtag to example labtag-->
        ( ~WHATProdAsPotKind|~AnaphoricTerm ) / (of|(\()? / (~AnaphoricTerm)? /
{ANAPHORIC_PRODUCT: ~LabTag} / ((#CM)? / {ANAPHORIC_PRODUCT:
~LabTag})* / (\))? / ( (to|of) / (~WHATProdAsPotKind|~AnaphoricTerm) /
{ANAPHORIC_PRODUCT: ~LabTag})? / ((#CM|and)? / {ANAPHORIC_PRODUCT:
~LabTag})*
        <!-- EX: masstag of the white solid -->
        ~ComplexValues / of / ~WHATProdAsAnaphoric
</concept>

<!-- This concept matches the material between commas or parentheses in phrases like -->
<!-- EX: to give, after drying with namtag, the title compound -->
<concept name="~Interphrase" level="1" display="never">
        ~Delimiter / (#CS|#IN) / (ANY|~NAME)* / ~Delimiter
```

~Delimiter / (^having / a)? / (m\.p\.|mp) / (of)? / ~ValTag / ~Delimiter
\( / (#CS|#IN) / (ANY|~NAME)* / \)
\( / (^having / a)? / (m\.p\.|mp) / (of)? / ~ValTag / \)
</concept>

<concept name="~TechnicalMention" display="never" level="1">
    <!-- SR, 2003-04-30: desired ... -->
    <!-- SR, 2003-05-06: ( in / total )? added -->
    <!-- ( in / total )? / (~ComplexValues / (\%)? / of)? / (:desired)? / {PRODUCT: (~NAME)} / (of)? / (#JJ)* / (~ComplexValues)? -->
    <!-- SR, 2003-05-23: ~ValTag ... -->
    <!-- SR, 2003-05-28: crystalline ... -->
    <!-- SR, 2003-06-03: title -->
( (~ValTag|~ComplexValues) / (\%)? / of )? / (the)? / (:desired|crude|crystalline)? / (title)? / {PRODUCT: (~NAME)} / (of)? / (#JJ)* / (~ComplexValues)?
    <!-- SR, 2003-03-21: but ... -->
    <!-- SR, 2003-05-06: treated ... -->
be / :charged / with / (~ComplexValues / (\%)? / of)? / ( pure )? / {REACTANT: (~NAME)} / (of)? / (#JJ)* / (~ComplexValues)?
be / :treated / with / (~ComplexValues / (\%)? / of)? / ( pure )? / {REACTANT: (~NAME)} / (of)? / (#JJ)* / (~ComplexValues)?
</concept>

<concept name="~GenericMention" display="never" level="1">
~AnaphoricMention / ANY / ~ComplexValues
~ComplexValues / ANY / ~AnaphoricMention
    <!-- EX: precipitate of namtag -->
{KIND_OF_PRODUCT: ~WHATProdAsPotKind} / of / (#AT|#DT) / ~TechnicalMention
~TechnicalMention / as / {KIND_OF_PRODUCT: ~WHATProdAsPotKind}
    <!-- namtag (labtag) -->
{PRODUCT: ~NAME} / \( / ~LabTag / \)
</concept>

<!-- SR, 2003-03-21: never -> whenreferenced -->
<concept name="~CompoundMention" display="whenreferenced" level="1">
~TechnicalMention
~GenericMention
~AnaphoricMention
    <!-- namtag, namtag and namtag -->
    <!-- SR, 2003-06-03: error with ~Delimiter corrected -->
(~AnaphoricMention|~TechnicalMention) / (~Delimiter / (~AnaphoricMention|~TechnicalMention))* / (~Delimiter)? / (or|and) / (AnaphoricMention|~TechnicalMention)
    <!-- SR, 2003-12-03 -->
( numtag )? / ( \. )? / {PRODUCT: ~NAME} / ( ~RefTag )? / ( (~Delimiter)? / ( numtag )? / ( \. )? / {PRODUCT: ~NAME} / ( ~RefTag )? )+
</concept>

</component>

PRODUCT_Constituent.scp

```xml
<?xml version = '1.0'?>

<!-- sc version = 'V1.20.0009' date = '2003-12-17' -->
<!-- copyright>(c) copyright 2001, MDL</copyright -->

<component>
<!-- utility chemical concepts -->
<concept name="~LabTag" display="never">
        labtag
</concept>

<!-- SR, 2003-05-19 -->
<concept name="~BezTag" display="never">
        beztag
</concept>

<!-- SR, 2003-05-06 -->
<concept name="~IgnLabTag" display="never">
        ignlabtag
</concept>

<concept name="~NamTag" display="never">
        namtag
</concept>

<!-- SR, 2003-05-19 -->
<concept name="~ClassTag" display="never">
        classtag
</concept>

<!-- SR, 2003-05-19 -->
<concept name="~SufTag" display="never">
        suftag
</concept>

<!-- SR, 2003-05-13 -->
<concept name="~NamTagAll" display="never">
        namtag
        ignnamtag
        labtag
        <!-- ignlabtag -->
</concept>

<!-- SR, 2003-12-03 -->
<concept name="~RefTag" display="always" autonomous="true">
        ( \( )? / reftag / ( \) )?
```

```
</concept>

<!-- SR, 2003-05-14 -->
<!-- <concept name="~PropTag" display="never"> -->
<!--     (proptag)+ -->
<!--     n / D / numtag / (\.)? / numtag / numtag -->
<!--     m\.p\. / (#CM)? / proptag -->
<!-- </concept> -->

<!-- SR, 2003-05-13 -->
<concept name="~MeassurementCompounds" searchOn="form" display="always" autonomous="true">
        {HELPER: (~NamTagAll)} / activity / of
        ( in|under ) / #AT / atmosphere / of / ({HELPER: (~NamTagAll)})?
        ( in|under ) / #AT / ({HELPER: (~NamTagAll)})? / atmosphere
        ( adsorbed|absorbed ) / ( in|on|onto ) / ( valtag / of )? / ({HELPER:
(~NamTagAll)})
        <!-- SR, 2003-08-27 -->
        {HELPER: (~NamTagAll)} / ( tube | column )
        <!-- SR, 2003-08-27 -->
        ( containing | with ) / a / trace / of / {HELPER: (~NamTagAll)}
        <!-- SR, 2003-11-06, 2003-12-03 -->
        ( acidified | extracted ) / ( by | with ) / {HELPER: (~NamTagAll)}
        <!-- SR, 2003-11-19 -->
        #AT / air / in / #AT / system
        <!-- SR, 2003-12-03 -->
        in / #AT / small / amount / of / {HELPER: (~NamTagAll)}
        <!-- SR, 2003-12-12 -->
        #AT / resulting / light-sensitive / composition
        in / place / of / {HELPER: (~NamTagAll)}
</concept>

<!-- SR, 2003-05-15: -->
<concept name="~AlternativeCompounds" searchOn="form" display="always" autonomous="true">
        but / :using / {REACTANT: (~NamTag)}
</concept>

<!-- SR, 2003-03-11: Additional fragments to cover unneeded compounds -->
<!-- SR, 2003-03-21: crystallized ... -->
<!-- SR, 2003-04-30: partitioned ... -->
<concept name="~HelperCompounds" display="always" autonomous="true">
        <!-- SR, 2003-05-06: times... -->
        <!-- (:crystallized|:recrystallized) / (~WhatMultipliers)? / from / {HELPER:
(~NamTagAll)} / ( V / {HELPER: (~NamTagAll)} )? -->
        <!-- SR, 2003-05-14, 20, 28 -->
```

(:crystallized|:recrystallized|recrystallization|:eluding|(elution / :using)) / (~WhatMultipliers)? / (from|with)? / ( a / mixture / of )? / {HELPER: (~NamTagAll)} / ( ( V|and ) / {HELPER: (~NamTagAll)} )?

between / ( ( ~WhatModifiers )? / (valtag)? / {HELPER: (~NamTagAll)} / ( \( / valtag / \) )? ) / ( ( #CM )? / ( and )? / ( ~WhatModifiers )? / (valtag)? / {HELPER: (~NamTagAll)} / ( \( / valtag / \) )? )*

:dissolved / in / (valtag)? / (of)? / {SOLVENT: (~NamTagAll)}

(:diluted | :washed | :dried) / (~WhatMultipliers)? / (with|over) / {HELPER: (~NamTagAll)}

<!-- SR, 2003-05-06 -->
{HELPER: (~NamTagAll)} / ( :sweep | :flushed )
under / ( #AT / (gentle)? / stream / of )? / {HELPER: ~NamTagAll}
<!-- SR, 2003-05-14 -->
{HELPER: (~NamTagAll)} / (contaminant)? / that / be / :formed
<!-- SR, 2003-06-03, 04 -->
(:cooled|:heated)/ (at / ignvaltag )? / (in|with)? / #AT / (#JJ)? / ~NamTagAll / ( \- / ~NamTagAll )? / bath
<!-- SR, 2003-12-12 -->
on / #AT / ~NamTagAll / plate
</concept>

<!-- SR, 2003-05-23: autonomous="true" -->
<concept name="~ValTag" display="never" autonomous="true">
    (valtag)+
    ignvaltag
    <!-- SR, 2003-05-23: can't work here! -->
    <!-- yield / (\:|\=|of) / valtag -->
    valtag / yield
    V / \- / numtag
    (valtag|ignvaltag) / x / numtag
    numtag / \- / (valtag|ignvaltag)
    \: / (valtag|ignvaltag)
    numtag / (\:|x) / (valtag|ignvaltag)
    purity / (of)? / (valtag|ignvaltag)
    (valtag|ignvaltag) / purity
    <!-- ... Idee ... \( / namtag / #CM / valtag / \) -->
    <!-- SR, 2003-06-04 -->
    :corresponding / to / valtag
</concept>

<concept name="~ComplexValues" display="always" autonomous="true">
    <!-- SR, 2003-05-08: "numtag" added -->
    \(? / ( (less|more|greater|higher|lower) / than )? / ( numtag / #CM )? / ~ValTag / ((\,|\;|and|of|x|X|V) / ~ValTag)* / \)?
    <!-- SR, 2003-05-13: -->
    \( / ~ValTag / (#CM / ~ValTag)? / in / {SOLVENT: ~NamTagAll} / \)
    <!-- SR, 2003-05-15: -->

\( / ~ValTag / #CM / (reference / example)? / (~LabTag|numtag) / ( \( / (~LabTag|numtag) / \) )? / \)

\( / (#RB)? / ~ValTag / of / #AT / ~ValTag / solution / in / {SOLVENT: ~NamTagAll} / \)

<!-- SR, 2003-05-19: -->

\( / ~ValTag / in / {SOLVENT: namtag|numtag} / ( \, / ~ValTag)+ / \)

<!-- AH, 2002-10-31: ~ addiert. -->
<!-- SR, 2003-05-20: ANAPHORIC_REACTANT ... -->
<!-- SR, 2003-11-06: "about" added -->

~ValTag / \( / (about)? / ~ValTag / ( ( \,|\;|and|of|x|X|V ) / ~ValTag )* / \) / ( of / #AT / {ANAPHORIC_REACTANT: (compound|product)})?

<!-- the assumption is that the namtags in the brackets in ex. like a mixture of distilled namtag ( valtag namtag / valtag namtag / valtag namtag ) are no reactants or products -->

\( / ~ValTag / namtag / (V / ~ValTag / namtag)* / \)
</concept>

<concept name="~NAME" display="never" autonomous="true">
    <!-- SR, 2003-05-14 -->
    (~NamTag)+
    (~ClassTag)+
    (~LabTag)+
    (~SufTag)+
    (~BezTag)+
    <!-- SR, 2003-08-27: numtag excluded -->
    <!-- (numtag)+ -->
    <!-- Labtag now represented by ~AntecedentExpression -->
    <!-- (~NamTag)+ / (~LabTag|~IgnLabTag)? -->
</concept>

<concept name="~Catalyst" display="always" autonomous="true">
    <!-- SR, 2003-05-21: Assumed that a catalyst can be detected very specifically. -->
    (:using)? / ({CATALYST: ~NAME} / and)? / {CATALYST: ~NAME} / (as)? / (#AT)? / catalyst
    #AT / catalytic / amount / of / {CATALYST: ~NAME}
    with / #AT / {CATALYST: ~NAME} / ( V / {CATALYST: ~NAME} )? / catalyst
    <!-- SR, 2003-11-06: added "traces of" -->
    (:catalysed|:catalyzed) / by / ( trace / of )? / {CATALYST: ~NAME} / ( and / {CATALYST: ~NAME} )?
    in / #AT / presence / of / {CATALYST: ~NAME}
</concept>

</component>

PRODUCT_GrammaticalConstituent.scp

```xml
<?xml version = '1.0'?>

<!-- sc version = 'V1.20.0009' date = '2003-12-17' -->
<!-- copyright>(c) copyright 2001, MDL</copyright -->

<!-- This file is now very short since all Barrier concepts have been deleted. -->

<component>

; utility grammatical concepts
<concept name="~Delimiter" display="never" autonomous="true">
     #CM
     \:
</concept>

</component>
```

PRODUCT_REACTANT_What.scp

```xml
<?xml version = '1.0'?>

<!-- sc version = 'V1.20.0009' date = '2003-12-17' -->
<!-- copyright>(c) copyright 2001, MDL</copyright -->

<component>

<!-- SR, 2003-05-06: Definition of pure equipment (interferes with contexts). -->
<concept name="~WhatEquipment" searchOn="form" display="always"
autonomous="true">
        in / #AT / ( numtag / ( \- )? / ml )? / (reaction)? / flask
</concept>

<!-- SR, 2003-05-06: Definition of pure equipment (interferes with contexts). -->
<concept name="~WhatCompanies" searchOn="form" display="never"
autonomous="true">
        Aldrich
        Strem / Chemicals
</concept>

<!-- SR, 2003-06-03 -->
<concept name="~WhatPatOffices" searchOn="form" display="never"
autonomous="true">
        U\.S\. / Pat
</concept>

<!-- SR, 2003-05-08: Definition of modifications to compounds. -->
<concept name="~WhatModifier" searchOn="form" display="never"
autonomous="true">
        :saturated
        :aqueous
        :aq\.
</concept>

<!-- SR, 2003-05-15: -->
<concept name="~WhatMultipliers" searchOn="form" display="never"
autonomous="true">
        (once|twice|( (several|numtag) / :times))
</concept>

<concept name="~WhatModifiers" searchOn="form" display="never"
autonomous="true">
        ( ~WhatModifier ) / ( ~WhatModifier )?
</concept>

<!-- SR, 2003-05-20 -->
```

```xml
<concept name="~WhatReferences" searchOn="form" display="never" autonomous="true">
        ( reference )? / example / labtag
</concept>

<concept name="~WhatProduct" searchOn="form" display="never" autonomous="true">
        <!-- SR, 2003-02-28: only on form, singular -->
        <!-- needles, crystals as plural only -->
        a / slurry / of
        <!--added acid because of results of SR-->
        acid
        agent
        bar
        block
        brick
        component
        <!--added concentrate-->
        concentrate
        crystals
        cube
        diastereoisomer
        diastereomer
        <!--added emulsion-->
        emulsion
        enantiomer
        epimer
        extract
        fibre
        film
        flake
        foam
        fraction / (a|beta)?
        gas
        <!--added gel-->
        gel
        glass
        gum
        isomer
        leaf
        liquid
        mass
        <!--added optional complex because of results of SR-->
        material / (complex)?
        microprism
        mix
        molecule
        needles
        oil
``` oligomer
<!-- SR, 2003-11-07: paste -->
paste
phase
plate
platelet
polymer
<!--added since found in corpus-->
copolymer
powder
<!--added since found in corpus-->
precipitate#NN
coprecipitate#NN
preparation
prism
rod
<!--added salt because of results of SR-->
salt
semisolid
sequence
<!-- SR, 2003-08-29 -->
sirup
slab
structure
</concept>

<concept name="~WhatReactant" searchOn="form" display="never" autonomous="true">
        <!--solution : SR, 2003-02-28: removed -->
        suspension
</concept>

<!-- SR, 2003-03-19: solution needed for other resolution -->
<concept name="~WhatReactantInvis" searchOn="form" display="never" autonomous="true">
        solution
</concept>

<concept name="~WhatReactantOrProduct" searchOn="form" display="never" autonomous="true">
        <!-- residue : SR, 2003-02-28: removed -->
        <!-- SR, 2003-03-21: title added -->
        ( end | title )? / compound
        filtrate
        <!-- SR, 2003-02-28: preceding, final -->
        <!-- SR, 2003-08-27: title -->
        <!-- SR, 2003-08-29: obtained -->
        <!-- SR, 2003-11-19: desired -->
        (end|reaction|target|head|preceding|final|title|obtained|desired)? / product

```
<!-- mixture : SR, 2003-02-28: removed -->
<!-- added derivative -->
derivative | derivate
solid
substance
substrate
</concept>

<!-- SR, 2003-03-19: same trick as above -->
<!-- SR, 2003-03-21: of -->
<concept name="~WhatReactantOrProductInvis" searchOn="form" display="never" autonomous="true">
residue
<!-- SR, 2003-08-27: "resulting" added -->
(resulting)? / mixture / ( of )?
</concept>

<concept name="~WHATProdAsAnaphoricHeader" display="always" autonomous="true">
(~WhatProduct|compound) / ignlabtag / ( \. | \, )
</concept>

<concept name="~WHATProdAsAnaphoric" display="never" autonomous="true">
<!-- SR, 2003-05-08: "title" removed because covered earlier -->
<!-- (#RBC)? / (#AT)? / (titled|#JJ)* / {ANAPHORIC_PRODUCT: (~WhatProduct|~WhatReactantOrProduct)} -->
<!-- SR, 2003-02-28: desired -->
<!-- SR, 2003-05-08: "title" removed because covered earlier -->
<!-- SR, 2003-05-14: "as product name" added -->
(#RBC)? / (#AT)? / (titled|desired|#JJ)* / {ANAPHORIC_PRODUCT: (~WhatProduct|~WhatReactantOrProduct)} / ( of / {PRODUCT: (namtag)})?
<!-- SR, 2003-08-29: be - identify -->
(#RBC)? / (#AT)? / (titled|desired|#JJ)* / {ANAPHORIC_PRODUCT: (~WhatProduct|~WhatReactantOrProduct)} / (which|#CM|( be / identify )) / (on / :standing)? / (:crystallized / as)? / (#AT)? / (:desired)? / {PRODUCT: (namtag)}
<!-- SR, 2003-06-02 -->
(#RBC)? / (#AT)? / (titled|desired|#JJ)* / {ANAPHORIC_PRODUCT: (~WhatProduct|~WhatReactantOrProduct)} / :containing / ( {PRODUCT: (namtag)} / \( / valtag / \) / (and)? / (\,)? )*
</concept>

<!-- Elements of the WHAT-List that do not get the role ANAPHORIC_PRODUCT but can potentially function as KIND_OF_PRODUCT-->

<concept name="~WHATProdAsPotKind" display="never" autonomous="true">
<!-- SR, 2003-03-19: too generally -->
<!-- (#RBC)? / (#AT)? / (#JJ)* / (~WhatProduct|~WhatReactantOrProduct) -->
(as)? / (#AT)? / (#JJ)* / (~WhatProduct|~WhatReactantOrProduct)
```

```
</concept>

<concept name="~WHATReactAsAnaphoric" display="never" autonomous="true">
    <!-- SR, 2003-05-20: too unspecific ... optional * removed -->
    (#RBC)? / (#AT)? / (title|titled|#JJ) / {ANAPHORIC_REACTANT:
(~WhatReactant|~WhatReactantOrProduct)}
    <!-- SR, 2003-05-08, -14: but... -->
    (#RBC)? / (#AT)? / (title|titled|#JJ)* / {ANAPHORIC_PRODUCT:
(~WhatReactant|~WhatReactantOrProduct)} / be / :collected
    <!-- SR, 2003-03-19: inserted; 2003-05-15: corrected -->
    (#RBC)? / (#AT)? / (title|titled|#JJ)* / (~WhatReactantInvis)
    (#RBC)? / (#AT)? / (title|titled|#JJ) / (~WhatReactantOrProductInvis)
</concept>

<!-- SR, 2003-03-19 -->
<concept name="~WHATReactAsPotKind" display="never" autonomous="true">
    (#RBC)? / (#AT)? / (#JJ)* / (~WhatReactant|~WhatReactantOrProduct)
</concept>

<!-- SR, 2003-03-20 -->
<concept name="~WHATProdPointer" display="never" autonomous="true">
    (there|{ANAPHORIC_PRODUCT: (it)})
</concept>

</component>
```

PRODUCT_Extraction.scp

```xml
<?xml version = '1.0'?>

<!-- sc version = 'V1.20.0009' date = '2003-12-17' -->
<!-- copyright>(c) copyright 2001, MDL</copyright -->

<!-- Taking the grammar V1.00.0000 from 30.10.01 as a basis we now combine the
constructions for the various verb contexts into one file. This will allow for an easier
maintenance where the different forms (passive, gerund, ...) for the different verbs will be
handled together. -->

<component>

<!-- CONTEXT active -->
<!--active verbforms with the product right to it -->
<concept name="~ActProductVerbRight" level="1" display="never" autonomous="true">
    <!-- SR, 2003-11-14: ~Comprising -->
    (~AffordAct|~Comprising|~ConvertIntoAct|~ExtractAct|~ToFormAct|~GiveAct|~I
solateAct|~LeaveAct|~ObtainAct|~PrecipitateAct|~PrepareAct|~ProduceAct|~ProvideAct|
~RecoverAct|~ResultInAct|~YieldAct)
</concept>

<!--active verbforms with the product left to it and product-participle-constructions -->
<!--EX: until a white solid forms -->
<!--EX: product formed -->
<!-- SR, 2003-03-11: ~RemainAct added -->
<!-- SR, 2003-05-06: ~CrystallizePass added -->
<concept name="~ActProductVerbLeft" level="1" display="never" autonomous="true">
    (~AffordParticiple|~ConvertFromParticiple|~CrystallizePass|~FormAct|~FormParti
ciple|~IsolateParticiple|~ObtainParticiple|~PrecipitateParticiple|~PrepareParticiple|~Produ
ceParticiple|~ProvideParticiple|~RecoverParticiple|~RemainAct|~SeparatePass|~YieldParti
ciple)
</concept>

<concept name="~CProductAct" level="1" display="always">
    <!-- SR, 2003-03-19: ~WhatReactantOrProductInvis -->
    <!-- SR, 2003-08-27: ~WHATProdAsPotKind; ( ~ValTag / of ) added -->
    ~ActProductVerbRight / (ANY|~Interphrase|~WhatReactantOrProductInvis|(
~ValTag / of ))* / ~CompoundMention / ( ~WHATProdAsPotKind )?
    ~CompoundMention / ~ActProductVerbLeft
</concept>

<!-- CONTEXT passive -->
<!-- ObtainFrom seems dangerous because there are many examples where a reactant -->
<!-- is mentioned that was "obtained from" a previous reaction -->
<concept name="~PassProductVerbMain" level="1" display="never"
autonomous="true">
```

```
        (~AffordPass|~ConvertFromPass|~ExtractPass|~FormPass|~IsolatePass|~ObtainPas
s|~ObtainFrom|~PrecipitatePass|~ProducePass|~ProvidePass|~RecoverPass|~SynthesizePa
ss|~YieldPass)
</concept>

<!-- SR, 2003-05-28: moved from ~PassProductVerb, separated. -->
<concept name="~PassProductVerbSpec" level="1" display="never" autonomous="true">
        (~PreparePass)
</concept>

<concept name="~CProductPass" level="1" display="always">
        <!-- SR, 2003-05-19: ~Delimiter -->
        ~CompoundMention / ANY / (~Interphrase|~Delimiter)? / ANY /
(~PassProductVerbMain|~PassProductVerbSpec)
        <!-- SR, 2003-05-28: very specific; rest is found via ~ComplexValue etc -->
        ~CompoundMention / ~PassProductVerbSpec / {REACTANT: ~NAME} / ( and /
{REACTANT: ~NAME} )?
        <!-- SR, 2003-05-13 -->
        <!-- (there|{ANAPHORIC_PRODUCT: (it)}) / ~PassProductVerb /
(ANY|~Interphrase)* / ~CompoundMention -->
        <!-- SR, 2003-05-20 -->
        ~WHATProdPointer / (~PassProductVerbMain|~PassProductVerbSpec) /
(ANY|~Interphrase)* / ~CompoundMention
        <!-- SR, 2003-08-29 -->
        ~CompoundMention / be / identify / as / {PRODUCT: ~NAME}
</concept>

<!-- SR, 2003-05-23: Hide ... -->
<concept name="~CProductPassHide" level="1" display="always" autonomous="false">
        mixture / of / ~CompoundMention / ANY / (~Interphrase|~Delimiter)? / ANY /
~PassProductVerb
</concept>

<!-- Ex: The yield is x -->
<concept name="~CProductKopula" level="1" display="always">
        ~ProductNoun / (ANY|~Interphrase)* / ^be / ~CompoundMention
</concept>

<concept name="~CProductNominalization" level="1" display="always">
        <!-- Ex: The generation of x -->
        ~ProductNoun / (#AT)? / (#NN|#JJ)* / ~CompoundMention
        <!-- Ex: namtag formation begins -->
        {PRODUCT: ~NAME} / ~ProductNoun / ~VerbInNominalizationContext
        <!-- SR, 2003-08-29 -->
        {PRODUCT: ~NAME} / in / the / form / of / (#NN|#JJ)* / ~CompoundMention
</concept>

<!-- SR, 2003-03-17: new rule added. -->
```

```
<!-- SR, 2003-03-21: Prepared, produced ... -->
<!-- Covers the citation of compounds from earlier locations. -->
<concept name="~CProductObtainedInExample" level="1" display="always">
    {REACTANT: (~NAME)} / ( \( )? /
(~ObtainParticipleExample|~PrepareParticipleExample|~ProduceParticipleExample)
</concept>

</component>
```

REACTANT_CompoundMention.scp

```xml
<?xml version = '1.0'?>

<!-- sc version = 'V1.20.0009' date = '2003-12-17' -->
<!-- copyright>(c) copyright 2001, MDL</copyright -->

<component>

<concept name="~AnaphoricMentionReact" display="never" level="3">
        <!-- If it is wanted to extract an anaphoric term alone than the concept
~AnaphoricTerm has to be added here. -->
        ~WHATReactAsAnaphoric
        <!-- Ex: the title namtag -->
        {ANAPHORIC_REACTANT: (title|titled) / ~NAME}
        <!-- Ex: the namtag product -->
        <!-- SR, 2003-05-28: get only the ~NAME itself, not including the
~WHATReactAsPotKind -->
        {ANAPHORIC_REACTANT: ~NAME} / ~WHATReactAsPotKind
        <!-- Ex: the namtag labtag -->
        ~NAME / {ANAPHORIC_REACTANT: ~LabTag }
        <!-- Ex: the title product of example labtag -->
        <!-- Ex: the compounds of example labtag to example labtag -->
        ( ~WHATReactAsPotKind|~AnaphoricTerm ) / (of|(\())? / (~AnaphoricTerm) /
{ANAPHORIC_REACTANT: ~LabTag} / ((#CM)? / {ANAPHORIC_REACTANT:
~LabTag})* / (\))?     / ( (to|of) / (~WHATReactAsPotKind|~AnaphoricTerm) /
{ANAPHORIC_REACTANT: ~LabTag})? / ((#CM|and)? /
{ANAPHORIC_REACTANT: ~LabTag})*
</concept>

<concept name="~TechnicalMentionReact" display="never" level="3">
        <!-- (~ComplexValues)? / (\%)? / (of)? / {REACTANT: (~NAME)} / (of)? / (#JJ)*
/ (~ComplexValues)? -->
        <!-- SR, 2003-05-06 -->
        <!-- SR, 2003-05-13: adjective introduced. ~ValTag added. -14: article added -->
        <!-- SR, 2003-06-02: "milled" (why not #JJ?) -->
        ({REACTANT: (~NAME)} / and)? / (~ValTag|~ComplexValues)? / (\%)? / (of)? /
(#AT)? / (#JJ)? / (:milled)? / {REACTANT: (~NAME)} / (\()? / (~LabTag)? / (\))? / (of)? /
(#JJ)* / (~ValTag|~ComplexValues)
        (~ValTag|~ComplexValues) / (\%)? / (of)? / (#AT)? / (#JJ)? / (:milled)? /
{REACTANT: (~NAME)} / (\()? / (~LabTag)? / (\))? /(of)? / (#JJ)* /
(~ValTag|~ComplexValues)?
        <!-- SR, 2003-05-19: -->
        :hydrogenated / over / (~ValTag|~ComplexValues)? / (\%)? / (of)? / {CATALYST:
(~NAME)} / (of)? / (#JJ)* / (~ComplexValues)?
        {REACTANT: (~NAME)} / ~RefTag
</concept>
```

```
<concept name="~SolventMentionReact" display="never" level="3">
    <!-- SR, 2003-05-06: "( {REACTANT: (~NAME)} )?" added -->
    <!-- SR, 2003-05-08: ( {REACTANT: (~NAME)} )? / in / (ANY |
~ComplexValues)* / {SOLVENT: ~NAME} / (ANY | ~ComplexValues)* -->
    <!-- SR, 2003-05-20: "( {REACTANT: (~NAME)} / (and|or) )? /" added -->
    <!-- SR, 2003-06-02: "~ValTag" added -->
    ( {REACTANT: (~NAME)} / (and|or) )? / ( {REACTANT: (~NAME)} )? / in /
(ANY | (~ComplexValues|~ValTag))* / {SOLVENT: ~NAME} / (ANY |
~ComplexValues)* / ({REACTANT: (~NAME)} )?
      in / (#AT|#DT)? / (#JJ|#NN)* / solvent / (ANY | ~ComplexValues)* / ( (comprise|
( compose / of)) / (ANY | ~ComplexValues)* / {SOLVENT: ~NAME} / (ANY |
~ComplexValues)* )*
      in / (#AT|#DT)? / (#JJ|#NN)* / solvent / (ANY|((contain|comprise)? / (of)? /
~ComplexValues))* / (of)? / {SOLVENT: ~NAME}
    <!-- SR, 2003-06-03 -->
      (:eluding)? / solvent / ~ValTag / {SOLVENT: ~NAME}
      ~WhatReactant / (of)? / (ANY|{REACTANT: (~NAME)}|~ComplexValues)* / in
/ (#AT|#DT)? / (#JJ)* / {SOLVENT: ~NAME}
</concept>

<!-- SR, 2003-03-21: never -> always -->
<concept name="~RCompoundMention" display="always" autonomous="true"
level="3">
    ~AnaphoricMentionReact
    ~TechnicalMentionReact
    ~SolventMentionReact
    <!-- SG: here we need to reference the ...Mention concepts of the -->
    <!--    Reactant Grammar, not the Product Grammar -->
    <!-- SR, 2003-06-03: error with ~Delimiter corrected -->
    (~AnaphoricMentionReact|~TechnicalMentionReact) / (~Delimiter /
(~AnaphoricMentionReact|~TechnicalMentionReact))* / (~Delimiter)? / (or|and) /
(~AnaphoricMentionReact|~TechnicalMentionReact)
</concept>

</component>
```

REACTANT_Extraction.scp

```xml
<?xml version = '1.0'?>

<!-- sc version = 'V1.20.0009' date = '2003-12-17' -->
<!-- <copyright>(c) copyright 2001, MDL </copyright> -->

<component>

<!-- all concepts that need to be skipped by the ~CReactant Rule -->

<concept name="~ProductExpr" display="never" level="3">
        ~ConvertFromPass
        ~ConvertIntoPass
        ~ConvertFromParticiple
        ~ExtractAct
        ~ExtractPass
        ~ExtractParticiple
        ~FormAct
        ~FormPass
        ~FormParticiple
        ~GiveAct
        ~IsolateAct
        ~IsolatePass
        ~IsolateParticiple
        ~LeaveAct
        ~ObtainPass
        ~ObtainAct
        ~ObtainParticiple
        <!-- SR, 2003-03-14: necessary ~ObtainParticipleExample ? -->
        ~ObtainFrom
        ~PrecipitateAct
        ~PrecipitateParticiple
        ~PrecipitatePass
        ~PrepareAct
        ~PrepareParticiple
        ~PreparePass
        <!-- SR, 2003-03-21: necessary ~PrepareParticipleExample ? -->
        ~ProduceAct
        ~ProducePass
        ~ProduceParticiple
        ~ProvideAct
        ~ProvidePass
        ~ProvideParticiple
        ~ResultInAct
        ~SynthesizePass
        ~SynthesizeFrom
        ~YieldAct
```

```xml
            ~YieldPass
            ~YieldParticiple
            ~ActProductVerbRight
            ~ActProductVerbLeft
            ~PassProductVerbMain
            ~PassProductVerbSpec
            ~Delimiter
            ;~PostBarrier
            ;~WHATProd
            ~CProductAct
            ~CProductPass
            ~CProductKopula
            ~CProductNominalization
</concept>

<!-- all assumed reactant verbs -->
<concept name="~ReactantVerb" display="never" autonomous="true" level="3">
        <!-- SR, 2003-05-08: place -->
        <!-- SR, 2003-05-14: mix -->
        (add|boil|bubble|charge|convert|cool|dissolve|drop|evaporate|feed|heat|hold|introduce|mix|place|pour|react|reflux|resuspend|stir|stirr|suspend|treat|warm)
</concept>

<!-- these expressions are taken from the document written by MS -->
<concept name="~ReactantExpr" display="never" autonomous="true" level="3">
        be / use / as / starting / material
        the / yield / from
        addition / of
</concept>

<!-- the single extraction rule for reactants -->
<concept name="~CReactant" display="always" level="4">
        ~RCompoundMention / (and|#CM)? / (then)? /
(~RCompoundMention|~IPhrase|~ComplexValues|ANY|~ProductExpr)* /
(~ReactantVerb|~ReactantExpr) /
(~RCompoundMention|~IPhrase|~ComplexValues|ANY|~ProductExpr)*
        <!-- SR, 2003-05-13, 14 -->
        ({SOLVENT: (~NAME)} / free)? / ({REACTANT: (~NAME)} | ~RCompoundMention) / (have)? / be / ~ReactantVerb
        <!-- SR, 2003-05-08: In a list, not all compounds must be given with ~ComplexValues -->
        ( {ANAPHORIC_PRODUCT: (it)} / ~PreparePassReactant)? / (~ReactantVerb) / (with)? / {REACTANT: (~NAME)} / (and|#CM)? / (then)?
</concept>
</component>
```

While the embodiments shown and described herein are fully capable of achieving the objects of the invention, it is to be understood that these embodiments are shown only for the purpose of illustration and not for the purpose of limitation, and that variations will be apparent to those skilled in the art in light of the foregoing description.

What is claimed is:

1. A computer implemented method for processing via software text documents and extracting chemical data therein, comprising:
    identifying, by a computer, one or more chemical compounds within a text document, said text document is an XML-type document, wherein said identifying is performed by software without human interaction;
    tagging, by said computer, each of said one or more chemical compounds with a tag that designates it as a chemical name;
    tagging, by said computer, at least one anaphor in said text document with a tag that designates said at least one anaphor as a chemical name;
    identifying, by said computer, at least one chemical reaction within said text document by:
        analyzing each phrase in said text document that includes chemical name tags, to determine a pattern of words and chemical name tags in said phrases,
        for each phrase, matching at least one predefined pattern, assigned to one of at least two priority levels, to said pattern of words and chemical name tags in said phrase, wherein each predefined pattern is associated with chemical roles in place of chemical name tags and wherein said at least one predefined pattern is applied to the text in order of its priority level, and
        determining a chemical role for each chemical name tag in said text document based on said at least one predefined pattern matched to each phrase in said text document;
    extracting via software said at least one chemical reaction that includes at least one chemical name and at least one chemical role for said at least one chemical name; and
    storing via software said extracted at least one chemical reaction in a database.

2. The method of claim 1, wherein at least some of said chemical compounds are described by their names.

3. The method of claim 1, wherein at least some of said chemical compounds are uniquely described by molecular formulas.

4. The method of claim 1, wherein said step of identifying one or more chemical compounds within a text document comprises comparison to a dictionary of chemical name fragments.

5. The method of claim 1, further comprising translating one or more of said chemical compounds into a respective chemical structure, wherein said translating is performed by software without human interaction, wherein said chemical structure is represented by a connection table.

6. The method of claim 1, wherein said chemical roles comprise: starting material, reagent, solvent, catalyst, and product.

7. The method of claim 1, wherein identifying at least one chemical reaction within said text document comprises identifying a yield of product within said reaction.

8. The method of claim 1, further comprising translating said extracted at least one chemical reaction into a format that allows storing said extracted at least one chemical reaction in said database.

9. The method of claim 1, further comprising identifying and tagging atomistic properties within said text document.

10. The method of claim 9, wherein said atomistic properties comprise one or more of: molecular formulas, numbers, ranges of numbers, physical values, labels, and references within text.

11. The method of claim 1, further comprising analyzing text based on line breaks, numbering schemes, and keywords.

12. The method of claim 1, further comprising validating said at least one identified chemical reaction by comparing one or more of the number of educts, the number of products or the number of unidentified compounds, against a predefined threshold.

13. Apparatus for processing text documents and extracting chemical data therein, comprising:
    means for identifying, by a computer, one or more chemical compounds within a text document;
    means for tagging each of said one or more chemical compounds with a tag that designates it as a chemical name;
    means for tagging at least one anaphor in said text document with a tag that designates said at least one anaphor as a chemical name;
    means for identifying at least one chemical reaction within said text document comprising:
        means for analyzing each phrase in said text document that includes chemical name tags, to determine a pattern of words and chemical name tags in said phrases,
        means for matching, for each phrase, at least one predefined pattern to said pattern of words and chemical name tags in said phrase, wherein each predefined pattern is associated with chemical roles in place of chemical name tags, and
        means for determining a chemical role for each chemical name tag in said text document based on said at least one predefined pattern matched to each phrase in said text document; and
    means for validating said at least one identified chemical reaction by comparing one or more of the number of educts, the number of products or the number of unidentified compounds, against a predefined threshold;
    means for extracting said at least one chemical reactions and storing said extracted said at least one chemical reaction in a database.

14. Apparatus in accordance with claim 13, wherein said means for identifying one or more chemical compounds comprise comparison means, for comparing to a dictionary of chemical name fragments.

15. Apparatus in accordance with claim 13, wherein means for identifying at least one chemical reaction comprises means for identifying a yield of product within a reaction.

16. Apparatus in accordance with claim 13, further comprising means for translating said extracted at least one chemical reaction into a format convenient for storing said extracted tagged information in said database.

17. The apparatus of claim 13, further comprising means for checking the identified chemical reactions operable to:
    detect reaction centers; and
    map atoms of one or more starting materials to the atoms of one or more products.

* * * * *